(12) United States Patent
Kopsky et al.

(10) Patent No.: US 11,285,099 B2
(45) Date of Patent: *Mar. 29, 2022

(54) TOPICAL PHENYTOIN FOR USE IN THE TREATMENT OF PERIPHERAL NEUROPATHIC PAIN

(71) Applicants: Topical Innovations B.V., Amsterdam (NL); Jan Marius Keppel Hesselink, Bosch en Duin (NL)

(72) Inventors: David Jos Kopsky, Amsterdam (NL); Jan Marius Keppel Hesselink, Bosch en Duin (NL)

(73) Assignees: Topical Innovations B.V., Amsterdam (NL); Jan Marius Keppel Hesselink, Bosch en Duin (NL)

(*) Notice: Subject to any disclaimer, the term of this patent is extended or adjusted under 35 U.S.C. 154(b) by 111 days.

This patent is subject to a terminal disclaimer.

(21) Appl. No.: 16/467,179

(22) PCT Filed: Dec. 6, 2017

(86) PCT No.: PCT/NL2017/050814
§ 371 (c)(1),
(2) Date: Jun. 6, 2019

(87) PCT Pub. No.: WO2018/106107
PCT Pub. Date: Jun. 14, 2018

(65) Prior Publication Data
US 2020/0276106 A1   Sep. 3, 2020

(30) Foreign Application Priority Data
Dec. 6, 2016 (NL) ...................... 2017931

(51) Int. Cl.
| | |
|---|---|
| A61K 9/00 | (2006.01) |
| A61K 9/06 | (2006.01) |
| A61K 31/4166 | (2006.01) |
| A61K 47/06 | (2006.01) |
| A61K 47/10 | (2017.01) |
| A61K 47/14 | (2017.01) |
| A61P 25/02 | (2006.01) |
| A61P 29/00 | (2006.01) |

(52) U.S. Cl.
CPC ............ *A61K 9/0014* (2013.01); *A61K 9/06* (2013.01); *A61K 31/4166* (2013.01); *A61K 47/06* (2013.01); *A61K 47/10* (2013.01); *A61K 47/14* (2013.01); *A61P 25/02* (2018.01); *A61P 29/00* (2018.01)

(58) Field of Classification Search
CPC .... A61K 31/4166; A61K 9/0014; A61K 9/06; A61K 47/06; A61K 47/10; A61K 47/14; A61K 47/44; A61K 45/06; A61P 25/00; A61P 25/02; A61P 29/00; A61P 17/00; A61P 3/08

See application file for complete search history.

(56) References Cited

U.S. PATENT DOCUMENTS

| | | | | |
|---|---|---|---|---|
| 6,113,921 A | * | 9/2000 | Friedman | A61P 25/08 424/400 |
| 2004/0101582 A1 | | 5/2004 | Wolicki | |
| 2004/0191276 A1 | | 9/2004 | Muni | |
| 2006/0034910 A1 | | 2/2006 | Patel et al. | |
| 2009/0022779 A1 | | 1/2009 | Kelly et al. | |
| 2011/0275137 A1 | * | 11/2011 | Matsuyama | A61K 38/51 435/232 |
| 2013/0184351 A1 | | 7/2013 | Ciullo | |
| 2013/0317009 A1 | * | 11/2013 | Frosch | A61P 29/00 514/217 |
| 2014/0141056 A1 | | 5/2014 | Kubo et al. | |

FOREIGN PATENT DOCUMENTS

| | | |
|---|---|---|
| CN | 101069692 B | 4/2011 |
| CN | 106075556 A | 11/2016 |
| EP | 0193855 B1 | 7/1990 |
| KR | 10-2012-0086957 A | 8/2012 |
| WO | 98/07447 A1 | 2/1998 |
| WO | 01/00191 A2 | 1/2001 |

(Continued)

OTHER PUBLICATIONS

Carneiro, et al "Topical phenytoin versus EUSOL in the treatment of non-malignant chronic leg ulcers" East Afr Med J. Mar. 2003;80(3):124-9).

Cheshire "Trigeminal neuralgia: a guide to drug choice" CNS Drugs. Feb. 1997;7(2):98-110).

Deuis et al. "Analgesic effects of clinically used compounds in novel mouse models of polyneuropathy induced by oxaliplatin and cisplatin" Neuro Oncol. Oct. 2014;16(10):1324-32).

Tremont-Lukats et al. "Anticonvulsants for neuropathic pain syndromes: mechanisms of action and place in therapy" Drugs. Nov. 2000;60(5): 1029- 52).

Yang et al., "Suboptimal Treatment of Diabetic Peripheral Neuropathic Pain in the United States," Pain Medicine, vol. 16, (2015), pp. 2075-2083.

(Continued)

*Primary Examiner* — Sarah Pihonak
(74) *Attorney, Agent, or Firm* — TraskBritt

(57) ABSTRACT

The present disclosure relates to pharmaceutical compositions containing phenytoin or phenytoin sodium for use in topical pain relief. Use of the pharmaceutical composition of the disclosure reduces peripheral neuropathic pain. The topical pharmaceutical compositions of the disclosure containing phenytoin or phenytoin sodium, surprisingly reduce peripheral neuropathic pain considerably, especially and preferably in the conditions, characterized by a low to moderate grade of peripheral neurogenic inflammation, such as small fiber neuropathy, diabetic neuropathy, chronic idiopathic axonal polyneuropathy, post-herpetic neuralgia, trigeminus neuralgia, chemotherapy induced polyneuropathy, traumatic neuropathies, compression neuropathies, and infectious neuropathies in remission, according to the disclosure.

18 Claims, 1 Drawing Sheet

(56) References Cited

FOREIGN PATENT DOCUMENTS

| WO | 02/92056 A1 | 11/2002 |
| WO | 2006/013084 A1 | 2/2006 |
| WO | 2008/079727 A2 | 7/2008 |
| WO | 2010/036937 A1 | 4/2010 |
| WO | 2015/089050 A1 | 6/2015 |

OTHER PUBLICATIONS

Yajnik et al., Phenytoin as a Coanalgesic in Cancer Pain, Journal of Pain and Symptom Management, Elsevier, vol. 7, No. 4, (1992), XP023115482, pp. 209-213.

Vincent et al., "Biology of Diabetic Neuropathy," Handbook of Clinical Neurology, vol. 115, (2013), pp. 591-606.

Uceyler et al., "Elevated Proinflammatory Cytokine Expression in Affected Skin in Small Fiber Neuropathy," Neurology, vol. 74, (2010), pp. 1806-1813.

Uceyler et al., "Differential Gene Expression of Cytokines and Neurotrophic Factors in Nerve and Skin of Patients With Peripheral Neuropathies," Journal of Neurology, vol. 262, (2015), pp. 203-212.

Uceyler et al., "Differential Expression of Cytokines in Painful and Painless Neuropathies," Neurology, vol. 69, (2007), pp. 42-49.

Tse et al., "Skin Permeability and Pharmacokinetics of Diclofenac Epolamine Administered by Dermal Patch in Yorkshire-Landrace Pigs," Journal of Pain Research, vol. 5, (2012), pp. 401-408.

Serajuddin et al., "Influence of pH on Release of Phenytoin Sodium From Slow-Release Dosage Forms," Journal of Pharmaceutical Sciences, vol. 82, No. 3, (Mar. 1993), pp. 306-310.

Rashidi et al., "The Effect of Phenytoin Cream in Comparison with Betadine Solution on Episiotomy Pain of Primiparous Women," Journal of Caring Sciences, vol. 1, (2012), XP055380888, pp. 61-65.

Rajabally et al., "Hereditary and Inflammatory Neuropathies: A Review of Reported Associations, Mimics and Misdiagnoses," Journal of Neurology Neurosurgery & Psychiatry, vol. 87, (2015), 11 pages.

Petersen et al., "Diclofenac Epolamine (Flector) Patch: Evidence for Topical Activity," Clinical Drug Investigation, vol. 29, No. 1, (2009), 1-9.

Moulin et al., "Pharmacological Management of Chronic Neuropathic Pain: Revised Consensus Statement From the Canadian Pain Society," Pain Research and Management, vol. 19, (2014), pp. 328-335.

Moore et al., "Gabapentin for Chronic Neuropathic Pain and Fibromyalgia in Adults," Cochrane Database of Systematic Reviews, Issue 4, (2014), 124 pages.

McQuay et al., "Anticonvulsant Drugs for Management of Pain: A Systematic Review," Bmj, vol. 311, (Oct. 21, 1995), pp. 1047-1052.

Lund et al., "Pharmacokinetics of Single and Multiple Doses of Phenytoin in Man," European Journal of Clinical Pharmacology, vol. 7, Issue 2, (Mar. 1974), pp. 81-86.

Korinth et al., "Potential of the Octanol-Water Partition Coefficient (logP) to Predict the Dermal Penetration Behaviour of Amphiphilic Compounds in Aqueous Solutions," Toxicology Letters, vol. 215, (2012), pp. 49-53.

Kopsky et al., "Neuropathic Pain as a Result of Acromegaly, Treated With Topical Baclofen Cream," Journal of Pain Symptom Management, vol. 46, (2013), pp. e4-e5.

Kopsky et al., "High Doses of Topical Amitriptyline in Neuropathic Pain: Two Cases and Literature Review," Pain Practice, vol. 12, (2011), pp. 148-153.

Kopsky et al., "Central Neuropathic Pain in a Patient With Multiple Sclerosis Treated Successfully With Topical Amitriptyline," Case Reports in Medicine, vol. 2012, (2012), Article ID 471835, 3 pages.

Keskin et al., "Doxepin Incorporated into a Dermatologic Cream: an Assessment of Both Doxepin Antipruritic Action and Doxepin Action as an Inhibitor of Papules, In Allergen and Histamine-Caused Pruritus," Allergol Immunopathol (Madr), vol. 27, No. 5, (1999), pp. 265-270.

Jensen et al., "Anticonvulsants in Neuropathic Pain: Rationale and Clinical Evidence," European Journal of Pain, vol. 6, (Suppl. A), (2002), pp. 61-68.

Jay et al., Neuropathic Pain: Etiology, Pathophysiology, Mechanisms, and Evaluations, Disease-a-Month, vol. 60, (2014), pp. 6-47.

Hesselink et al., "Vulvodynia and Proctodynia Treated With Topical Baclofen 5 % and Palmitoylethanolamide," Archives of Gynecology Obstet, vol. 290, (2014), pp. 389-393.

Hesselink et al., "Treatment of Chronic Regional Pain Syndrome Type 1 With Palmitoylethanolamide and Topical Ketamine Cream: Modulation of Nonneuronal Cells," Journal of Pain Research, vol. 6, (2013), pp. 239-245.

Hearn et al., "Desipramine for Neuropathic Pain in Adults," Cochrane Database of Systematic Reviews, vol. 9, (2014), 33 pages.

Glinn et al., "Urinary Concentations of Topically Administered Pain Medications," Journal of Analytical Toxicology, vol. 41, (2016), pp. 127-133.

Gharibian et al., "Compliance and Persistence of Antidepressants Versus Anticonvulsants in Patients With Neuropathic Pain During the First Year of Therapy," Clinical journal of pain, vol. 29, (2013), pp. 377-381.

Finnerup et al., "Pharmacotherapy for Neuropathic Pain in Adults: A Systematic Review and Meta-Analysis," Lancet Neurology, vol. 14, (2015), pp. 162-173.

Ellis et al., "Neuroinflammation and the Generation of Neuropathic Pain," British Journal of Anaesthesia, vol. 111, (2013), pp. 26-37.

Derry et al., "Topical Lidocaine for Neuropathic Pain in Adults," Cochrane Database of Systematic Reviews, Issue 7, (2014), 12 pages.

David J. Kopsky, "Phenytoin in Topical Formulations Augments Pain Reduction of Other Topically Applied Analgesics in the Treatment of Trigeminal Neuralgia," Journal of Clinical Anesthesia, vol. 38, (2017), XP029963147, pp. 154-155.

Database WPI CN1110141, Oct. 18, 1995, XP002778531.

Callaghan et al., "The Importance of Rare Subtypes in Diagnosis and Treatment of Peripheral Neuropathy: A Review," JAMA Neurology, vol. 72, (2015), pp. 1510-1518.

Bos et al., "The 500 Dalton Rule for the Skin Penetration of Chemical Compounds and Drugs," Experimental Dermatology, vol. 9, (2000), pp. 165-169.

Baron et al., "Peripheral Input and Its Importance for Central Sensitization," Annals of Neurology, vol. 74, (2013), pp. 630-636.

Bailey DN., "Percutaneous Absorption of Tricyclic Antidepressants: Amitriptyline, Nortriptyline, Imipramine, and Desipramine," Journal of Analytical Toxicology, vol. 14, No. 4, (1990), pp. 217-218.

Babaei et al., "Enhanced Skin Penetration of Lidocaine Through Encapsulation into Nanoethosomes and Nanostructured Lipid Carriers: A Comparative Study," Pharmazie, vol. 71, No. 5, (2016), pp. 247-251.

Alan Israel, "Topical Gel for the Treatment of a Refractory Leg Ulcer", International Journal of Pharmaceutical Compounding, vol. 7, No. 3, (2003), XP055380945, 3 pages.

Chadda et al. "Double Blind Study of the Effects of Diphenylhdantoin Sodium on Diabetic Neuropathy" Assoc Physicians India. (May 1978) 26(5): 403-6.

Ellenberg "Unremitting Painful Diabetic Neuropathy" JAMA (May 1977) vol. 237, No. 18.

Gogtay et al. "A Randomized, Crossover, Assessor-Blind Study of the Bioequivalence of a Single Oral Dose of 200 mg of Four Formulations of Phenytoin Sodium in Healthy, Normal Indian Volunteers" Therapeutic Drug Monitoring (April 2003) vol. 25—Issue 2—p. 215-220.

Saudeket al. "Phenytoin in the treatment of diabetic symmetrical Polyneuropathy" Phenytoin in diabetic polyneuropathy, vol. 22, No. 2, pp. 196-199 (Mar. 1977).

Taylor et al "Na+ channels as targets for neuroprotective drugs" Trends in Pharmacological Sciences, vol. 16, Issue 9, Sep. 1995, pp. 309-316.

Japanese Notice of Reasons for Refusal for Japanese Application No. 2019-531112, dated Oct. 4, 2021, 13 pages with English translation.

(56) References Cited

OTHER PUBLICATIONS

Chinese First Office Action for Chinese Application No. 201780082443.1, dated Jan. 6, 2022, 25 pages with translation.

* cited by examiner

TOPICAL PHENYTOIN FOR USE IN THE TREATMENT OF PERIPHERAL NEUROPATHIC PAIN

CROSS-REFERENCE TO RELATED APPLICATIONS

This application is a national phase entry under 35 U.S.C. § 371 of International Patent Application PCT/NL2017/050814, filed Dec. 6, 2017, designating the United States of America and published in English as International Patent Publication WO 2018/106107 A1 on Jun. 14, 2018, which claims the benefit under Article 8 of the Patent Cooperation Treaty to Dutch Patent Application Serial No. 2017931, filed Dec. 6, 2016.

TECHNICAL FIELD

The present disclosure concerns a pharmaceutical composition for use in the treatment of peripheral neuropathic pain. More specifically, the disclosure concerns a pharmaceutical composition for use in the treatment of peripheral neuropathic pain, wherein the peripheral neuropathic pain is characterized by a low to moderate grade of peripheral neurogenic inflammation, and wherein the pharmaceutical composition is administered topically. Furthermore, the present disclosure concerns the stratification of patients suffering from peripheral neuropathic pain, therewith increasing the efficacy of pharmaceutical compositions for use in the treatment of peripheral neuropathic pain.

BACKGROUND

Pain results from noxious stimulation of nerve endings. Peripheral neuropathic pain is caused by damage of neural structures from the peripheral nervous system, such as damage to peripheral nerve endings in the skin (e.g., from nociceptors). These damaged nerve endings can generate impulses in the absence of stimulation, can be hypersensitive to normal stimulation, and/or can be triggered by remaining local inflammatory stimulation. Even a very small number of damaged and overactive small nerve fibers in the epidermis are sufficient to trigger peripheral neuropathic pain. Examples are peripheral neuropathic pain due to diabetic neuropathy, post-herpetic neuralgia, trigeminal neuralgia, chronic idiopathic axonal polyneuropathy and chemotherapy-induced polyneuropathy.

Peripheral nerve damage initially leads to a pathological state which causes reduction in pain threshold (resulting in clinical symptoms such as allodynia), increased response to noxious stimuli (hyperalgesia), and/or an increased response duration (persistent pain). Patients suffering from peripheral neuropathic pain generally are treated with oral analgesics, such as antidepressants (e.g., amitriptyline and duloxetine) or gabapentinoids (e.g., gabapentin and pregabalin). Unfortunately, oral neuropathic pain medication has been associated with low response rates, drug-drug interactions, side effects, as well as tolerability problems and compliance problems. This all leads to suboptimal neuropathic pain relief.

Two most commonly used topical compounds in the treatment of neuropathic pain are capsaicin (a vanilloid receptor agonist and counter-irritant) and lidocaine (a membrane stabilizer). However, both topical capsaicin 0.025% to 0.075% as well as capsaicin 8% patch, have the disadvantage that application quite often induces intolerable side effects, such as increasing burning sensation, and often the treatment has to be combined with a local anesthetic to neutralize this side effect (G. W. Jay and R. L. Barkin (2014)). The topical lidocaine 5% patch, disclosed in U.S. Patent Application 2014/0141056 and in U.S. Patent Application 2013/0184351, needs to be replaced every 12 hours, cannot be used on wounds, ulcers, damaged or inflamed skin, commonly seen in patients with diabetic neuropathy, and might give problems in use when applied to toes, especially in elderly, because the patch has to be cut. Also other topical forms of lidocaine up to 8% in creams and gels are available on the market (S. Derry et al. (2014)). Yet no evidence from good quality randomized controlled trials is available to support the use of topical lidocaine to treat neuropathic pain, although some individual studies seem to indicate that topical lidocaine might be effective for relief of neuropathic pain (S. Derry et al. (2014)). However, the consensus amongst patients and their medical practitioners is that response rates of patients suffering from neuropathic pain to topical lidocaine and more generally to any neuropathic pain medication, both topically as well as orally, have remained quite unsatisfactory.

More and more it is felt that "neuropathic pain" is an insufficient container concept. "Neuropathic pain" is a collection of different pathological states which are characterized by various pathogenic processes. To expect that one drug will be effective in a series of different neuropathic pain syndromes is clearly a bridge too far. There is thus an urgent need for individualized treatment strategies for patients suffering from specific neuropathic pain syndromes. Furthermore, there is a strong need for treatment options with diminished side effects, or even better, without side effects, also when administered chronically, for example, a few times per day or week or month, for a period of days, weeks, months, years.

BRIEF SUMMARY

The current disclosure provides a treatment of peripheral neuropathic pain, preferably of peripheral neuropathic pain syndromes characterized by low to moderate grade of peripheral neurogenic inflammation.

A first aspect of the present disclosure relates to a pharmaceutical composition comprising an analgesic as the active pharmaceutical ingredient and a pharmaceutically acceptable carrier, wherein the analgesic is selected from phenytoin or a derivative, a prodrug, a stereoisomer, and/or a salt thereof, or any combination thereof, for use in the treatment of peripheral neuropathic pain.

In one embodiment, the pharmaceutically acceptable carrier in the pharmaceutical composition of the disclosure is a pharmaceutically acceptable carrier for topical use.

In one embodiment, the pharmaceutically acceptable carrier for topical use in the pharmaceutical composition of the disclosure is a pharmaceutically acceptable carrier for topical use on the skin.

In one embodiment, the pharmaceutical composition comprising an analgesic as the active pharmaceutical ingredient and a pharmaceutically acceptable carrier for topical use is a pharmaceutical topical composition for use in the treatment of peripheral neuropathic pain, wherein that use is the topical use in the treatment of peripheral neuropathic pain.

In one embodiment, the pharmaceutical composition comprising an analgesic as the active pharmaceutical ingredient and a pharmaceutically acceptable carrier for topical use is a pharmaceutical topical composition for use in the treatment of peripheral neuropathic pain, wherein that use is the topical use on intact skin of the treated person in the treatment of peripheral neuropathic pain.

In one embodiment, the pharmaceutical composition for use according to the disclosure is for use in the treatment of peripheral neuropathic pain, wherein the peripheral neuropathic pain is due to low to moderate grade of neurogenic inflammation selected from any one or more of: small fiber neuropathy (SFN), diabetic neuropathy type 1 and 2, chronic idiopathic axonal polyneuropathy (CIAP), post-herpetic neuralgia, trigeminus neuralgia, chemotherapy-induced polyneuropathy (CIPN), a traumatic neuropathy and an infectious neuropathy in remission.

In one embodiment, the pharmaceutical composition for use according to the disclosure is for use in the treatment of peripheral neuropathic pain, wherein the peripheral neuropathic pain is due to low to moderate grade of neurogenic inflammation selected from any one or more of: small fiber neuropathy (SFN), diabetic neuropathy type 1 and 2, chronic idiopathic axonal polyneuropathy (CIAP), post-herpetic neuralgia, trigeminus neuralgia, chemotherapy-induced polyneuropathy (CIPN), a traumatic neuropathy, compression neuropathy and an infectious neuropathy in remission.

A second aspect of this disclosure relates to a method for preparing a pharmaceutical composition for use in the treatment of peripheral neuropathic pain, comprising the steps of:
a. providing oil-soluble constituents at between 20° C. and 95° C., and separately providing water soluble constituents of a pharmaceutically acceptable carrier for topical use;
b. providing an analgesic selected from phenytoin or a derivative, a prodrug, a stereoisomer, and/or a salt thereof, or any combination thereof, preferably phenytoin or phenytoin sodium or a combination thereof;
c. mixing the oil-soluble constituents at between 20° C. and 95° C. of step a. by stirring, and separately, dissolving the water-soluble constituents of step a. in water, wherein the water is optionally heated to between 20° C. and 95° C. while dissolving the water-soluble constituents of step a., thereby providing an aqueous solution;
d. combining the mixed oil-soluble constituents of step c. with the aqueous solution of step c., wherein the temperature of the mixed oil-soluble constituents and the aqueous solution is about the same, preferably about 70° C., and mixing by stirring, thereby providing the pharmaceutically acceptable carrier for topical use; and
e. mixing the selected analgesic of step b. with the pharmaceutically acceptable carrier of step d. by adding the selected analgesic to the carrier while stirring for between 5 and 20 minutes, preferably at about 20° C.; and
f. optionally adjusting the pH of the aqueous solution to between 4.0 and 6.5 or to between 10.0 and 12.0.

A further aspect of the disclosure relates to a method for preparing a pharmaceutical composition for use in the treatment of peripheral neuropathic pain, comprising the steps of:
a. providing a pharmaceutically acceptable carrier for topical use, which pharmaceutically acceptable carrier is a cream;
b. providing an analgesic selected from phenytoin or a derivative, a prodrug, a stereoisomer, and/or a salt thereof, or any combination thereof, preferably phenytoin or phenytoin sodium or a combination thereof;
c. mixing the constituents of step a. and b. at a temperature of between 15° C. and 30° C., preferably about 18° C. in a high sheer mixer, preferably in the first half and 3 minutes at 500 rpm to 1000 rpm and subsequently 1 to 4 minutes at 1000 rpm to 2000 rpm;
d. repeating step c. for between 1 time and 8 times, preferably 3 times, with a pause of between 8 and 12 minutes, preferably 10 minutes between each round of mixing to let cool down the cream to room temperature; and
e. optionally adjusting the pH of the aqueous solution to between 4.0 and 6.5 or to between 10.0 and 12.0.

In one embodiment, in the method according to the disclosure, the pharmaceutical composition is a pharmaceutical topical composition, and the use is the topical use in the treatment of peripheral neuropathic pain.

In one embodiment, in the method according to the disclosure, the pharmaceutical composition is a pharmaceutical topical composition, and the use is the topical use on intact skin of the treated person in the treatment of peripheral neuropathic pain.

A third aspect of this disclosure relates to a pharmaceutical composition obtainable by the method of the disclosure.

In one embodiment, the pharmaceutical composition obtainable by the method of the disclosure contains between 3% and 15% by weight of the analgesic selected from phenytoin or a derivative, a prodrug, a stereoisomer, and/or a salt thereof, or any combination thereof, preferably phenytoin or phenytoin sodium or a combination thereof.

In one embodiment, the pharmaceutical composition obtainable by the method of the disclosure contains between 3% and 40% by weight of the analgesic selected from phenytoin or a derivative, a prodrug, a stereoisomer, and/or a salt thereof, or any combination thereof, preferably phenytoin or phenytoin sodium or a combination thereof.

A fourth aspect of the disclosure relates to a pharmaceutical composition for use in the treatment of peripheral neuropathic pain according to the disclosure, wherein the pharmaceutical composition is provided by the method of the disclosure or wherein the pharmaceutical composition is a composition of the disclosure.

Definitions

Unless defined otherwise, all technical and scientific terms used herein have the same conventional meaning as commonly understood by one of ordinary skill in the art to which this disclosure belongs.

The term "constituent" has its conventional meaning and here refers to a component or similarly an ingredient of, e.g., a pharmaceutically acceptable carrier, (e.g., for topical use.

The term "comprising" or "comprises" as used herein has its conventional meaning and here means that the list following is non-exhaustive and may or may not include any other additional suitable items, for example, one or more further feature(s), component(s) and/or ingredient(s) as appropriate.

The term "approximately" as used herein has its conventional meaning and here means that a certain effect or result can be obtained within a certain tolerance of which the skilled person knows how to obtain the tolerance, and here indicates a reasonable amount of tolerated deviation of the identified parameter value such that a/the end result is not significantly changed. This reasonable amount of deviation should be construed as including a deviation of at least ±5% of the identified parameter value, as long as this deviation does not negate the end result.

The term "about" as used herein has its conventional meaning and here means that a certain effect or result can be obtained within a certain tolerance of which the skilled person knows how to obtain the tolerance.

The term "cold" in combination with "mixed," "mix," "mixing," or the like, refers to the initial temperature at the start of the step of mixing two or more products, constituents, excipients, etc. Here, the term cold thus refers to a temperature of between 15° C. and 30° C., preferably between 15° C. and 25° C., such as about 18° C., room temperature, ambient temperature.

The term "peripheral neuropathic pain" as used herein has its conventional meaning and here is defined as pain arising as a direct or indirect consequence of a lesion or disease affecting the peripheral somatosensory system. Peripheral neuropathic pain as used herein, includes all types of peripheral neuropathic pain, caused by, for example, peripheral diabetic neuropathy type 1 or 2, induced by various noxious substances such as alcohol, caused by various deficiencies such as vitamin B1, B6 and/or B12 deficiency, various intoxications, such as hypervitaminosis B6, caused by hypothyroidism, chemotherapy-induced polyneuropathy (CIPN) (due to, e.g., paclitaxel or other taxane derivatives, vincristine or other vinca alkaloids, cisplatin or other platinum derivatives), drug-induced neuropathy, compounds for the treatment of infectious diseases (e.g., streptomycin, didanosine or zalcitabine), or caused by any other chemically toxic compound. Other peripheral neuropathies that can cause peripheral neuropathic pain include the following: small fiber neuropathy (SFN), hereditary motor and sensory neuropathies (HMSN), chronic inflammatory demyelinating polyneuropathy (CIDP), trigeminal neuralgia, post-herpetic neuralgia, intercostal neuralgia, entrapment neuropathies (e.g., carpal tunnel syndrome, tarsal tunnel syndrome, abdominal cutaneous nerve entrapment syndrome), sciatic pain, chronic idiopathic axonal polyneuropathy (CIAP), vulvodynia, proctodynia, neuropathy due to infectious disease conditions, such as post-polio syndrome, AIDS or HIV-associated, lyme-associated, Sjögren-associated, lymphomatous neuropathy, myelomatous neuropathy, carcinomatous neuropathy, vasculitic/ischaemic neuropathy and other mono- and polyneuropathies.

The term "neurogenic inflammation" as used herein has its conventional meaning and here is defined as an inflammation arising from the local release of inflammatory mediators produced by afferent neurons or produced by the tissues in close contact to these afferent neurons.

The term "epidermal formulation" as used herein refers to a topical formulation wherein the active pharmaceutical ingredient is not detectable in plasma, or is detectable to a lesser extent in plasma when compared to a different route of administration than topical administration of an epidermal formulation.

The term "individualized medicine" as used herein has its conventional meaning and here is a medical procedure that separates patients into different groups, with medical decisions, practices, interventions and/or products being tailored to the individual patient based on their predicted response or risk of disease.

The term "ex juvantibus" as used herein has its conventional meaning and here refers in medical contexts to the process of making an inference about disease causation from an observed response of the disease to a treatment.

The term "treatment" as used herein has its conventional meaning and here is to be considered in its broadest context.

The term "treatment" is intended to encompass topical administration of active compounds according to the disclosure that alleviate an undesired condition, and therapeutic administration to eliminate or reduce the extent or symptoms of the condition. Treatment does not necessarily imply that a subject is treated until total recovery.

The terms "analgesic" as used herein has its conventional meaning and here refers to a compound, an agent, a drug or a substance that reduce pain in its broadest context.

The term "topical formulation" as used herein has its conventional meaning and here refers to a formulation that may be applied to skin or mucosa with the aim that a therapeutically active compound penetrates in and/or through the skin.

The phrase "derivative, prodrug, stereoisomer, and/or salt thereof" as used herein has its conventional meaning and here refers to any pharmaceutically acceptable tautomer, salt, pro-drug, hydrate, solvate, metabolite or other compound which, upon administration to the subject, is capable of providing (directly or indirectly) the active compound concerned or a metabolite or residue thereof.

The term "solvate" as used herein has its conventional meaning and here refers to a complex of solute (e.g., active compound, salt of active compound) and solvent.

The term "derivative" as used herein has its conventional meaning and here refers to a compound that is derived from a similar compound by a chemical reaction. A derivative includes esters, amides and protonated forms of these agents. Derivatives of phenytoin are known in the art and, for example, encompass phenytoin-3-histidine (IUPAC name (S)-3-(2-amino-3-(1H-imidazol-4-yl) propanoyl)-5,5-diphenylimidazolidine-2,4-dione), the phenytoin derivatives such as those disclosed in U.S. Pat. No. 5,306,617, hybrids between phenytoin and thiosemicarbazide, 1,3,4-oxadiazole, 1,3,4-thiadiazole or 1,2,4-triazole, phenytoin with any one or more of the substituents selected from the group consisting of: diphenylmethane, 5-phenylhydantoin, phenylimidazolidine, alpha-amino acid or derivatives, 5-monosubstituted hydantoin, N-acyl urea, ureide, a monocyclic benzene moiety, benzenoid, dicarboximide, a carbonic acid derivative, a carboxylic acid derivative, azacycle, a hydrocarbon derivative, an organic oxide, an organo-oxygen compound, an organo-nitrogen compound, an organopnictogen compound, an organic oxygen compound, a carbonyl group, an organic nitrogen compound, and an aromatic heteromonocyclic compound (see, for example, www-.drugbank.ca/drugs/DB00252), to name a few phenytoin derivatives known by the person having ordinary skill in the art.

The term "prodrug" as used herein has its conventional meaning and here refers in its broadest sense to include those compounds which can be converted in vivo to the compound of interest (e.g., by enzymatic or hydrolytic cleavage). Examples thereof include esters, such as acetates of hydroxyl or thiol groups, as well as phosphates and sulphonates. Processes for acylating hydroxyl or thiol groups are known in the art (e.g., by reacting an alcohol (hydroxyl group), or thiol group, with a carboxylic acid.

The terms "phenytoin" and "5,5-diphenylimidazolidine derivate" as used herein has its conventional meaning and here refer to phenytoin, fosphenytoin, hydroxyphenytoin, 5-(3-hydroxyphenyl)-5-phenylhydantoin, 5-phenyl-5-(4-hydroxyphenyl)hydantoin glucuronide, ropitoin, ropitoin hydrochloride, 5-(2-hydroxyphenyl)-5-phenylhydantoin, 5-(3,4-dihydroxy-1,5-cyclohexadien-1-yl)-5-phenylhydantoin, N-aminodiphenylhydantoin, 5-(3,4-dihydroxyphenyl)-5-phenylhydantoin, PC-796, 5-p-methylphenyl-5-phenylhydantoin, 1-acetyl-3-acetoxy-5',5-diphenylhydantoin, 3-hydroxymethylphenytoin N,N-dimethylglycine ester, 3-(hydroxymethyl)phenytoin N,N-dimethylaminoethyl carbonate, 5-(4-hydroxy-3-methoxyphenyl)-5-phenylhydantoin, 3-pentanoyl-5,5-diphenylhydantoin, 3-(2-propylpentanoyl)-5,5-diphenylhydantoin, 5,5-bis(4-hydroxyphenyl) hydantoin, 3-(hydroxymethyl)phenytoin, phenytoin dihydrodiol, 4-aminophenytoin, N,N-dichlorophenytoin, diphenylthiohydantoin, diphenylhydantoin-3-phenyltricarbonylchromium ethyl acetate, 5,5-diphenylhydantoin-3-valerate-bovine serum albumin, phenytoin-1-methylnicotininate, 2-cyanoguanidinophenytoin, phenytoin-bis-hydroxyisobutyrate, N-acetylphenytoin, diphenylhydantoic acid, N'-3-oxymethylglucuronide phenytoin, diphenylhydantil, 5-(4'-fluorophenyl)-5-phenylhydantoin, Azumolene, 5,5-bis(4-trifluoromethylphenyl)hydantoin, 5,5-bis(4-methylphenyl)hydantoin, 5,5-bis(4-methoxyphenyl)hydantoin, 5-(4-methoxyphenyl)-5-phenylhydantoin, and 5-(4-dimethylaminophenyl)-5-phenylhydantoin, and other 5,5-diphenylimidazolidine or a derivative, prodrug, stereoisomer, and/or salt thereof.

Grading of Peripheral Neurogenic Inflammation in Peripheral Neuropathic Pain

Neurogenic inflammation is regarded as a model and inroad for understanding neuropathic pain and hyperalgesia in certain patient groups. Peripheral nerve damage causes the release of many pro-inflammatory mediators, including many autacoids, such as pro-inflammatory interleukins (IL) (e.g., IL-1β), tumor necrosis factor-α (TNF-α), bradykinin, substance P, calcitonin gene-related peptide, nerve growth factor, and prostaglandins, contributing to the "inflammatory soup" (A. Ellis and D. L. Bennett, 2013), and induce cellular oxidative/nitrosative stress, which promotes even more neuronal damage (A. M. Vincent et al., 2013). For example, in small fiber neuropathy (SFN) pro-inflammatory cytokines in the skin are considerably elevated compared to healthy controls (e.g., IL-6: 7-fold; IL-8: 5-fold) (N. Uceyler et al., 2010). Furthermore, patients with inflammatory neuropathies can be distinguished from those with low to moderate grade of peripheral neurogenic inflammation (e.g., CIAP and SFN), according to much higher levels of neuro-inflammatory markers, such as TNF-α and IL-2 levels (N. Uceyler et al., 2007). In line with this differentiation, many supporting details can be noted, such as that anti-inflammatory cytokine IL-10 gene expression has been found to be significantly lower in inflammatory neuropathies, than in non-inflammatory neuropathies (N, Uceyler et al., 2015). Also hereditary neuropathies show significantly lower levels of inflammatory cells and mediators, than inflammatory neuropathies (Y. A. Rajabally et al., 2016).

Moderate to high grade of peripheral neurogenic inflammation can result in severe disabling pathology and should be treated differently than low to moderate grade of peripheral neurogenic inflammation. The common effective treatments for moderate to high grade of peripheral neurogenic inflammation include corticosteroids, intravenous immunoglobulin (IVIGs), plasma exchange, and other immunosuppressive medications (B. C. Callaghan et al., 2015).

Three grades of peripheral neurogenic inflammation are defined for classifying peripheral neuropathic pain patients: no to low grade (group A), low to moderate grade (group B) and moderate to high grade (group C) of peripheral neurogenic inflammation. Low to moderate grade of peripheral neurogenic inflammation is found in disorders, such as small fiber neuropathy, diabetic neuropathy, chronic idiopathic axonal polyneuropathy, post-herpetic neuralgia, trigeminal neuralgia, chemotherapy-induced polyneuropathy, traumatic neuropathies, and infectious neuropathies in remission. Furthermore, low to moderate grade of peripheral neurogenic inflammation is found in compression neuropathies.

Patients suffering from peripheral neuropathic pain syndromes are divided in the three groups A, B and C with regard to the grade of peripheral neurogenic inflammation. Dividing the total patient population in groups based on the grade of peripheral neurogenic inflammation allows for patient stratification with regard to therapy to be applied. With regard to the disclosure related to patient stratification, these three distinguishable groups of patients are defined as the following grades:

Group A: No to Low Grade of Peripheral Neurogenic Inflammation

Hereditary neuropathies without a significant inflammatory component (e.g., uncomplicated hereditary motor and sensory neuropathies (HMSN), intoxication neuropathies, such as alcoholic neuropathies, drug-associated neuropathies, and neuropathies due to heavy metals or organic chemicals (diethylene glycol, arsenic), length-dependent sensorimotor axonal peripheral neuropathies due to vitamin deficiencies, such as vitamin B12 deficiency-associated polyneuropathy, and non-inflammatory metabolic induced neuropathies, such as hypothyroidism-associated polyneuropathy).

Group B: Low to Moderate Grade of Peripheral Neurogenic Inflammation

SFN, diabetic neuropathy type 1 and 2, CIAP, post-herpetic neuralgia, trigeminus neuralgia, CIPN, traumatic neuropathies, and infectious neuropathies in remission.

Furthermore, patients suffering from compression neuropathies also belong to the Group B grade, i.e., the low to moderate grade of peripheral neurogenic inflammation.

Group C: Moderate to High Grade of Peripheral Neurogenic Inflammation

Autoimmune neuropathies, such as caused by Morbus Sjögren, acute and subacute inflammatory demyelinating polyneuropathy, chronic inflammatory demyelinating polyradiculoneuropathy, vasculitis neuropathy, postsurgical inflammatory neuropathy, Guillain-Barre-Landy-Strohl syndrome, multifocal acquired demyelinating sensory and motor neuropathy, familial amyloid polyneuropathy, and infectious neuropathies during exacerbation.

The term "fingertip unit," or its abbreviation "FTU," has its regular scientific meaning, and throughout the specification FTU refers to the practical aid for dosing analgesic creams. An FTU is the amount of cream squeezed from the distal interphalangeal crease to the end of the finger (see FIG. 1). A streak of cream from a tube with a round opening with a diameter of 6 mm is approximately 0.6 gram; a streak cream from a tube with an opening with a diameter of 5 mm is approximately 0.5 gram. Generally, about 0.8 FTU cream is required for one foot of an adult and about 0.5 FTU cream is required for one hand. Relatively flexible dosing (e.g., the amount of drug comprised in between about 0.5 gram and 0.6 gram of a certain cream containing the drug; i.e., in an FTU) is allowed for administration of a drug on the skin, since reaching any detectable systemic concentrations of the active compound(s) is not the purpose of the administration of a drug through locally applying the drug in a cream on the skin.

DETAILED DESCRIPTION

Figure 1:
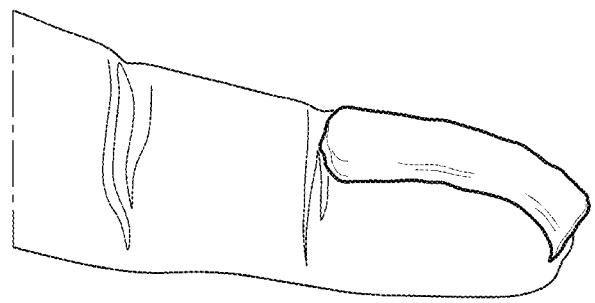
FIG. 1: Example of the amount of cream squeezed from the distal interphalangeal crease to the end of the finger, referred to as the "fingertip unit" (FTU), used as a practical aid for dosing analgesic creams.

This disclosure provides for an individualized treatment strategy for patients suffering from specific neuropathic pain syndromes, i.e., patient stratification for patients suffering from treatment-refractory neuropathic pain. This disclosure now surprisingly identifies an entire new field of application for topical phenytoin formulations and phenytoin sodium formulations of the disclosure, related to the now discovered analgesic effect of phenytoin and phenytoin sodium in peripheral neuropathic pain syndromes. It was surprisingly found that a sub-population of patients suffering from specific and identifiable peripheral neuropathic pain syndromes are full responders to a topical treatment in the form of a cream containing phenytoin and optionally containing a skin penetration enhancer according to the disclosure. Based on these clinical findings, it was determined that the common denominator amongst these patients responding to the therapy was the suffering from pain related to localized low to moderate grade of peripheral neurogenic inflammation, in and around the sensory afferents in the skin, the nociceptors and the tissue around these afferents. Furthermore, based on these clinical findings, it was also determined that the common denominator amongst these patients responding to the therapy was the suffering from pain related to low to moderate grade of peripheral neurogenic inflammation, in and around the sensory afferents in the skin, the nociceptors and the tissue around these afferents.

Therefore, it was desired to solve the problem of the treatment of such pain raising in and around the sensory afferents in the skin, where pathogenetic pathways can be located in the epidermal part of the skin, and it was surprisingly found that topically administered phenytoin indeed reduces peripheral neuropathic pain in the formulation, without giving rise to systemic side effects, as the topically applied phenytoin did not penetrate the blood, and no blood levels for phenytoin could be detected. Of course, it is appreciated by the skilled person that also parts of such pathogenic pathways related to pain in and around the sensory afferents in the skin, can be located in the epidermal part of the skin. The phenytoin formulation of the disclosure did not reach detectable concentrations of phenytoin in the plasma of patients treated with a pharmaceutical composition of the disclosure, as measured in 16 patients after application of phenytoin 10% cream of the disclosure. Even in one patient after application of 6.7 grams of phenytoin 10% cream (670 mg phenytoin), once daily during 25 days, and blood sampling 2.5 hours after last application, no detectable phenytoin in plasma was measured. This absence of the pharmaceutical ingredient phenytoin in blood is in clear contrast with other topical analgesic formulations, such as formulations containing the analgesic diclofenac epolamine (180 mg) in a 1.3% patch, lidocaine, amitriptyline, ketamine and doxepin cream. For further details, see the Examples section, below. Sixty-eight patients suffering from peripheral neuropathic pain were treated with a pharmaceutical composition of the disclosure and results of the treatment were followed and documented for weeks to years, dependent on the start of the administration of the pharmaceutical composition of the disclosure to each individual patient.

The topical formulation of diclofenac epolamine 1.3% patch for instance is designed to reach active drug levels in the muscles. Application of the patch on human skin and on pig skin resulted in measurable therapeutic plasma levels (mean peak concentration of about 1.8 ng/mL, and maximal measured concentration of about 6.1 ng/mL) [Petersen and Rovati, 2009; S. Tse et al., 2012]. This diclofenac epolamine 1.3% formulation reached comparable concentrations of diclofenac in muscles beneath the patch application site to corresponding tissue levels after oral administration (Cmax. values of 879 ng/mL after topical administration and 1160 ng/mL after oral administration [S. Tse et al., 2012]. Also doxepin 5% cream showed a plasma concentration of doxepin of maximal 47 ng/ml, with a mean of 10.8 ng/ml in 19 patients [G. Keskin et al., 1999]. The same holds true for a great number of other analgesics [M. A. Glinn et al., 2017].

Without wishing to be bound by theory, it is postulated herein that these pathogenic pathways in the skin are at least influenced, perhaps even dominated by inflammatory processes leading to chronification of pain after a peripheral nerve injury and/or after local intra- or sub-epidermal pathologies. Even discrete pathologies in the skin such as a small number of overactive aberrant small nerve fibers can already trigger peripheral neuropathic pain.

A first aspect of the present disclosure relates to a pharmaceutical composition comprising an analgesic as the active pharmaceutical ingredient and a pharmaceutically acceptable carrier, wherein the analgesic is selected from phenytoin or a derivative, a prodrug, a stereoisomer, and/or a salt thereof, or any combination thereof, for use in the treatment of peripheral neuropathic pain.

In one embodiment, the pharmaceutically acceptable carrier in the pharmaceutical composition of the disclosure is a pharmaceutically acceptable carrier for topical use.

In one embodiment, the pharmaceutically acceptable carrier for topical use in the pharmaceutical composition of the disclosure is a pharmaceutically acceptable carrier for topical use on the skin.

In one embodiment, the pharmaceutical composition comprising an analgesic as the active pharmaceutical ingredient and a pharmaceutically acceptable carrier such as a pharmaceutically acceptable carrier for topical use is a pharmaceutical topical composition for use in the treatment of peripheral neuropathic pain, wherein that use is the topical use in the treatment of peripheral neuropathic pain.

In one embodiment, the pharmaceutical composition comprising an analgesic as the active pharmaceutical ingredient and a pharmaceutically acceptable carrier for topical use is a pharmaceutical topical composition for use in the treatment of peripheral neuropathic pain, wherein that use is the topical use on intact skin of the treated person in the treatment of peripheral neuropathic pain.

In one embodiment, the pharmaceutical composition for use in the treatment of peripheral neuropathic pain according to the disclosure, is for the topical use in the treatment of peripheral neuropathic pain through the skin of the patient.

In one embodiment, the pharmaceutical composition for use in the treatment of peripheral neuropathic pain according to the disclosure, is for use in the treatment of a human.

In one embodiment, the pharmaceutical composition comprising an analgesic as the active pharmaceutical ingredient and a pharmaceutically acceptable carrier for topical use is a pharmaceutical topical composition for use in the treatment of peripheral neuropathic pain, wherein that use is the topical use on healthy intact skin of the treated person in the treatment of peripheral neuropathic pain. Here, intact skin and healthy intact skin have their common scientific meaning and here refer to non-injured skin free of, e.g., ulcers, wounds, lesions, cuts, and refer to skin comprising a closed outer layer of epidermis.

A further aspect of the present disclosure relates to a pharmaceutical composition comprising an analgesic as the active pharmaceutical ingredient and a pharmaceutically acceptable carrier, wherein the analgesic is selected from phenytoin or a derivative, a prodrug, a stereoisomer, and/or a salt thereof, or any combination thereof, for use in the treatment of peripheral neuropathic pain.

Yet a further aspect of the present disclosure relates to a pharmaceutical composition comprising an analgesic as the active pharmaceutical ingredient and a pharmaceutically acceptable carrier for topical use, wherein the analgesic is selected from phenytoin or a derivative, a prodrug, a stereoisomer, and/or a salt thereof, or any combination thereof, for topical use on the skin in the treatment of peripheral neuropathic pain of a human patient.

In one embodiment, the pharmaceutical composition for use according to the disclosure is for use in the treatment of peripheral neuropathic pain, wherein the peripheral neuropathic pain is due to low to moderate grade of neurogenic inflammation selected from any one or more of: SFN, diabetic neuropathy type 1 and 2, CIAP, post-herpetic neuralgia, trigeminus neuralgia, CIPN, a traumatic neuropathy and an infectious neuropathy in remission. In one embodiment, the pharmaceutical composition for use according to the disclosure is for use in the treatment of peripheral neuropathic pain, wherein the peripheral neuropathic pain is due to low to moderate grade of neurogenic inflammation selected from any one or more of: SFN, diabetic neuropathy type 1 and 2, CIAP, post-herpetic neuralgia, trigeminus neuralgia, CIPN, a traumatic neuropathy, compression neuropathy, and an infectious neuropathy in remission. It was found that the use of the pharmaceutical composition of the disclosure is particularly beneficial for patients suffering from peripheral neuropathic pain wherein the peripheral neuropathic pain is due to low to moderate grade of neurogenic inflammation selected from any one or more of: SFN, diabetic neuropathy type 1 and 2, CIAP, post-herpetic neuralgia, trigeminus neuralgia, CIPN, a traumatic neuropathy and an infectious neuropathy in remission. In addition, it was found that the use of the pharmaceutical composition of the disclosure is particularly beneficial for patients suffering from compression neuropathy. In numerous case studies (see the Examples section, below), the pharmaceutical composition of the disclosure proved to be efficient and efficacious when administered to at least patients suffering from peripheral neuropathic pain wherein the peripheral neuropathic pain is due to low to moderate grade of neurogenic inflammation selected from any one or more of: SFN, diabetic neuropathy type 1 and 2, CIAP, post-herpetic neuralgia, trigeminus neuralgia, CIPN, a traumatic neuropathy, compression neuropathy, and an infectious neuropathy in remission. See also Tables 11-13, below.

An embodiment of the disclosure is the pharmaceutical composition according to the disclosure for use in the treatment of peripheral neuropathic pain according to the disclosure, wherein the analgesic is phenytoin or phenytoin sodium or a combination thereof.

An embodiment of the disclosure is the pharmaceutical composition according to the disclosure for use in the treatment of peripheral neuropathic pain according to the disclosure, wherein the pharmaceutical composition comprises a pharmaceutically acceptable carrier for topical use selected from a cream, a gel, a dispersion, an emulsion, a foam, a mist, a mouth wash, a lotion, a salve, an ointment, a spray, an aerosol, an oil, a plaster, a patch, a suspension, or a suppository, preferably the pharmaceutically acceptable carrier for topical use is a cream.

Via an "ex juvantibus" approach, it was surprisingly found out that topical phenytoin cream of the disclosure reduces neuropathic pain very effectively in peripheral neuropathic pain syndromes characterized by low to moderate grade of peripheral neurogenic inflammation, such as SFN, diabetic neuropathy type 1 and 2, CIAP, post-herpetic neuralgia, trigeminus neuralgia, CIPN, and traumatic neuropathies. The topical phenytoin cream of the disclosure contains both phenytoin or phenytoin sodium and one or more skin penetration enhancers, such as decylis oleas, macrogol cetostearyl ether, or cetostearyl alcohol. Furthermore, via an "ex juvantibus" approach, it was surprisingly found out that topical phenytoin cream of the disclosure reduces neuropathic pain very effectively in peripheral neuropathic pain syndromes characterized by low to moderate grade of peripheral neurogenic inflammation, such as compression neuropathies, and an infectious neuropathy in remission.

Without wishing to be bound by theory, phenytoin, phenytoin sodium and their derivatives, prodrugs, stereoisomers and further salts thereof, and in particular phenytoin and phenytoin sodium, have properties particularly suitable for penetration of the skin, such as human skin, such as intact skin. That is to say, it is common general knowledge that molecules smaller than 500 Dalton can penetrate the stratum corneum of the skin. The stratum corneum barrier will allow the penetration of lipid soluble molecules more readily than water-soluble compounds. Water-soluble molecules may penetrate through an alternative way, the openings of sweat glands and hair follicles [Bos et al.]. All active pharmaceutical ingredients (APIs) used in the described pharmaceutical formulations of the disclosure have a molecular weight smaller than 500 Dalton. Therefore, without wishing to be bound by theory, skin penetration enhancers are not required for these mentioned APIs in order to be able to penetrate the stratum corneum of the skin to reach the nerve endings present in the next skin layer, the stratum granulosum. Since the more hydrophilic phenytoin sodium in cream has the same therapeutic effect as phenytoin cream (see Case 9 in the Examples section, below), lipophilicity and hydrophilicity of these compounds is not a limiting factor for these molecules smaller than 500 Dalton with regard to their ability to penetrate the (human) skin.

Penetration strategies seem not to be relevant for molecules with a positive log P (partition coefficient between octanol and water) and molecules smaller than 500 Dalton [Korinth et al., Bos et al.]. For example, Amitriptyline HCl 10% water solution (in total 2 mg amitriptyline) topically applied on the skin of mice resulted in effective transdermal absorption with in the lungs the highest detection of amitriptyline [Baily]. Another example: the cumulative percentage of permeated lidocaine comparing to penetration enhancement techniques (lidocaine into nanostructured lipid carriers or nanoethosomes) with control (hydroalcoholic lidocaine solution) did not reach statistical significance [Babaei et al.]. In Table 17, below, an overview of a series of exemplifying compounds is provided, the compounds known for their ability to penetrate the skin.

Indeed, referring to Table 16 and Case 1 to 14, below, it is clear that a pharmaceutical composition of the disclosure, comprising one or more skin penetration enhancers, or not comprising a skin penetration enhancer, are comparably efficient and efficacious in providing relief from peripheral neuropathic pain in patients after topical administration of the pharmaceutical composition on the skin of the human patient, according to the disclosure.

In order to optimally target and serve the individualized patient sub-group of the total patient population according to the principles of individualized medicine with the disclosure presented herein, based on the disclosure, it is now possible to distinguish three groups of patients suffering from peripheral neuropathic pain syndromes, depending on the grade of peripheral neurogenic inflammation. Characteristics of each of the three identifiable groups of patients are provided above, under "DEFINITIONS."

For patients characterized by the disease grade according to group A in general, in current practice neuropathic pain treatment consists of treatment with the classical groups of neuropathic pain analgesics, such as anti-epileptics and anti-depressants.

For patients characterized by the disease grade according to group B in general, in current practice neuropathic pain treatment consists of the classical groups of neuropathic pain analgesics, such as anti-epileptics and anti-depressants, and local treatments, such as high dose capsaicin patches and lidocaine patches.

For patients characterized by the disease grade according to group C in general, in current practice neuropathic pain treatment consists of the classical groups of neuropathic pain analgesics such as anti-epileptics and anti-depressants. In order to target the underlying disease, the effective treatments are commonly selected from, e.g., corticosteroids, intravenous immunoglobulin, plasma exchange, and other immunosuppressive medications.

Based on the current disclosure and without wishing to be bound by theory, it is now postulated that most of the signs and symptoms in the group of responders to treatment with topical phenytoin according to the disclosure, are induced via the process of (low to moderate grade of) peripheral neurogenic inflammation. In the light of the nowadays insights of individualized medicine it is recommended to target patient populations with new therapeutic modalities in such a way that an optimal match is secured between the therapy (i.e., topical treatment modalities with phenytoin and at least one skin penetration enhancer according to the disclosure) and the pathogenesis of the disease the patient is suffering from. The surprising finding of the disclosure that topical phenytoin responders are especially in the patient group characterized by low to moderate grade of peripheral neurogenic inflammation, provides an unprecedented and important contribution to individualized medicine in this field of peripheral neuropathic pain treatment.

An embodiment of the disclosure is the pharmaceutical composition according to the disclosure for use in the treatment of peripheral neuropathic pain according to the disclosure, wherein the peripheral neuropathic pain is selected from SFN, diabetic neuropathy type 1 and 2, CIAP, post-herpetic neuralgia, trigeminus neuralgia, CIPN, traumatic neuropathies, and infectious neuropathies in remission, or combinations thereof.

An embodiment of the disclosure is the pharmaceutical composition according to the disclosure for use in the treatment of peripheral neuropathic pain according to the disclosure, wherein the peripheral neuropathic pain is selected from SFN, diabetic neuropathy type 1 and 2, CIAP, post-herpetic neuralgia, trigeminus neuralgia, CIPN, traumatic neuropathies, compression neuropathies, and infectious neuropathies in remission, or combinations thereof.

An embodiment of the disclosure is the pharmaceutical composition according to the disclosure for use in the treatment of peripheral neuropathic pain according to the disclosure, wherein the peripheral neuropathic pain is of low grade to moderate grade.

An embodiment of the disclosure is the pharmaceutical composition according to the disclosure for use in the treatment of peripheral neuropathic pain according to the disclosure, wherein the pain is at least caused by localized low to moderate grade of peripheral neurogenic inflammation in and/or around the sensory afferents in the skin, and/or the nociceptors and/or the tissue around the afferents.

An embodiment of the disclosure is the pharmaceutical composition according to the disclosure for use in the treatment of peripheral neuropathic pain according to the disclosure, wherein the pain is at least caused by localized low to moderate grade of peripheral neurogenic inflammation in and around the sensory afferents in the skin, the nociceptors and the tissue around the afferents.

An embodiment of the disclosure is the pharmaceutical composition according to the disclosure for use in the treatment of peripheral neuropathic pain according to the disclosure, wherein the pain is at least caused by low to moderate grade of peripheral neurogenic inflammation in and around the sensory afferents in the skin, the nociceptors and the tissue around the afferents.

An embodiment of the disclosure is the pharmaceutical composition according to the disclosure for use in the treatment of peripheral neuropathic pain according to the disclosure, wherein the pain is at least caused by low to moderate grade of peripheral neurogenic inflammation in and/or around the sensory afferents in the skin, and/or the nociceptors and/or the tissue around the afferents.

Phenytoin is generally seen as a representative of first generation of anti-convulsants. The compound was first synthesized in 1908. The IUPAC name of phenytoin is 5,5-diphenylimidazolidine-2,4-dione; phenytoin is also referred to as diphenylhydantoin and 5,5-diphenyl-2,4-imidazolidinedione; one of several tradenames of phenytoin is phenytoin sodium, traded as Dilantin (sodium 5,5-diphenyl-2,4-imidazolidinedione). Phenytoin has been widely used as an anti-convulsant since its clinical introduction in 1938. Despite the long-term use of this compound, its molecular mechanism of action is still not fully understood. Surprisingly new indications have emerged since its use as an anti-convulsant, such as wound healing and bipolar depression. It is felt that the multiplicity of the pharmacological effects and mechanisms of action of phenytoin, (e.g., on ion channels and synaptic transmission, does not explain all its clinical effects.

Oral administered phenytoin has never shown convincing efficacy when applied as an oral analgesic and such oral treatment was never incorporated in treatment guidelines for the treatment of neuropathic pain (D. Moulin et al., 2014).

Use of topical phenytoin in the enhancement of wound healing is disclosed in U.S. Patent Application 2009/0022779. According to U.S. Patent Application 2009/0022779 Patent Application, phenytoin sodium is only dissolvable in water in significant amounts at a pH of approximately 12 or higher, which is not desirable for applications developed for wound healing, neither for applications on the skin. The lower the pH, the more the equilibrium between dissolved and undissolved phenytoin shifts to undissolved phenytoin (A. T. Serajuddin and C. I. Jarowski, 1993). In U.S. Patent Application 2009/0022779 5% by weight phenytoin sodium is mixed into an oil phase, and then a stabilizer and water are added while mixing. This way, a cream is provided comprising an oil phase serving as a phenytoin reservoir and comprising an aqueous phase containing dissolved phenytoin sodium. After application of the cream onto a wound, phenytoin is slowly released from the oil phase into the water phase. The targeted pH of this emulsified cream was between 7 and 10. In U.S. Patent Application 2009/0022779, yet another formulation is disclosed, for stabilizing phenytoin sodium in a Carbomer gel at a pH of 7.4, for use in the treatment of wounds.

The solubility of phenytoin sodium in water at 37° C. and in the pH range between 1 and 6 varies from 0.035 to 0.040 mg/mL and increases rapidly at higher pH to about 2 mg/ml (0.2% by weight) at pH 10, reaching a maximum solubility of about 140 mg/mL (14% by weight) at pH 11.1, which is in agreement with the $pK_\alpha$ value of 8.4 for phenytoin sodium ($K_\alpha$ is the dissociation constant) (A. T. Serajuddin and C. I. Jarowski, 1993).

Topically administered metallo ammonium phenytoin complexes combined with phenytoin or the sodium salt of phenytoin, has also been reported to possess antibacterial properties, as disclosed in U.S. Pat. No. 5,571,521, which antibacterial properties might be beneficial for wound healing.

It was surprisingly found that topical phenytoin cream was most effective when applied in the treatment of peripheral neuropathic pain syndromes belonging to group B (see above). This surprising finding provided the insight required in order to be able to dissect the whole spectrum of peripheral neuropathic pain syndromes in the above described three classes A, B and C. This stratification of patients based on disease sub-classes allowed for optimally defining and selecting target therapies and developing an individualized medicine approach in neuropathic pain patients, using topical formulations of phenytoin.

One embodiment of the disclosure is the pharmaceutical composition for use in the treatment of peripheral neuropathic pain according to the disclosure, wherein the pharmaceutical composition is administered between eight times daily to once every other day, preferably four, three, two or one times daily, more preferably once every other day.

One embodiment of the disclosure is the pharmaceutical composition for use in the treatment of peripheral neuropathic pain according to the disclosure, wherein the pharmaceutical composition is administered for a period of at least one day, preferably at least one week, more preferably at least one month, most preferably at least one year, preferably the pharmaceutical composition is chronically administered. Throughout the application, "chronically" is defined as for the rest of the life time (e.g., of a patient such as a human patient to whom a pharmaceutical composition of the disclosure is administered).

One embodiment of the disclosure is the pharmaceutical composition for use in the treatment of peripheral neuropathic pain according to the disclosure, wherein the unit dose of the analgesic is between 0.0005 gram and 1.0 gram, preferably between 0.005 gram and 0.6 gram, more preferably between 0.01 gram and 0.4 gram, most preferably about 0.25 gram. Thus, administering a single dose of the pharmaceutical composition of the disclosure delivers preferably between 0.0005 gram and 1.0 gram of the analgesic, preferably between 0.005 gram and 0.6 gram, more preferably between 0.01 gram and 0.4 gram, most preferably about 0.25 gram, according to the disclosure. Preferably, the analgesic in such single dose of the administered analgesic is phenytoin or phenytoin sodium or a combination thereof, according to the disclosure.

A new topical cream has been developed based on 5% and 10% phenytoin, which proved to be effective in the treatment of patients according to a case-series of patients suffering from neuropathic pain (see section EXAMPLES, below). All patients were refractory to other analgesics than phenytoin. In all patients of the examples Case 1-Case 9, as outlined in more detail below, phenytoin cream was effective in reducing pain at least by 30%, and in most cases by more than 50%, without any side effect, pointing to the absence of, or presence of only subclinical levels of, phenytoin in the plasma, and the tolerability was excellent. In most patients of the examples Case 10-Case 12, as outlined in more detail below, phenytoin cream was effective in reducing pain at least by 30%, and in most cases by more than 50%, without any side effect, pointing to the absence of, or presence of only subclinical levels of, phenytoin in the plasma, and the tolerability was excellent. The onset of analgesic action of the phenytoin creams of the disclosure is surprisingly very fast, within 10 to 30 minutes, (e.g., already at 15 minutes after the cream of the disclosure is administered to the skin, which fast onset excludes an analgesic effect of the phenytoin via the blood, and points to an epidermal mechanism of action of the pharmaceutical composition of the disclosure. In contrast, after oral administration of a composition comprising an active pharmaceutical ingredient of the prior art, peak plasma concentrations are reached only after 4 to 12 hours [L. Lund et al., 1974]. It is well known to the specialist in the field that, generally, APIs delivered orally are leading to a Cmax. value in plasma within a shorter period of time compared to delivery of the same API via topical formulations. The above context clearly supports the topical intra-epidermal mechanism of action of topical phenytoin in a cream of the disclosure.

It is established that the pharmaceutical composition for use in the treatment of peripheral neuropathic pain according to the disclosure, wherein the pharmaceutical composition comprises either phenytoin and wherein the pH of the composition is about 5, or phenytoin sodium and wherein the pH of the composition is about 11, are similarly or even equally effective in reducing peripheral neuropathic pain in patients, according to the disclosure.

One embodiment of the disclosure is the pharmaceutical composition for use in the treatment of peripheral neuropathic pain according to the disclosure, wherein the pharmaceutical composition comprises between 0.5% and 20% by weight analgesic, preferably phenytoin or phenytoin sodium or a combination thereof, preferably between 5% and 10% by weight, and wherein between 0.1 gram and 4 gram of the pharmaceutical composition is administered, preferably between 0.5 gram and 3.6 gram. These weight percentages relate to the total weight of the pharmaceutical composition of the disclosure.

One embodiment of the disclosure is the pharmaceutical composition for use in the treatment of peripheral neuropathic pain according to the disclosure, wherein the pharmaceutical composition comprises between 0.5% and 40% by weight analgesic, preferably phenytoin or phenytoin sodium or a combination thereof, preferably between 5% and 30% by weight, and wherein between 0.1 gram and 4 gram of the pharmaceutical composition is administered, preferably between 0.5 gram and 3.6 gram. The amounts of between 0.1 gram and 4 gram of the pharmaceutical composition, preferably between 0.5 gram and 3.6 gram, refer to the amount of pharmaceutical composition that is administered as a single dose to the patient, preferably administered topically to the skin, preferably the intact skin, of a human patient, according to the disclosure.

One embodiment of the disclosure is the pharmaceutical composition for use in the treatment of peripheral neuropathic pain according to the disclosure, wherein the carrier for topical use is a cream having a pH of between 4.0 and 6.5, preferably between 4.5 and 6.2, more preferably about 5.5. One embodiment of the disclosure is the pharmaceutical composition for use in the treatment of peripheral neuropathic pain according to the disclosure, wherein the carrier for topical use is a cream having a pH of between 10.0 and 12.0, preferably about 11.3.

A pharmaceutical composition for use in the treatment of peripheral neuropathic pain according to the disclosure having a pH of between 4.0 and 6.5 is preferred. It is common general knowledge that in general compositions applied to the skin of patients having such a pH are mild to the skin of patients, with regard to the pH of between 4.0 and 6.5.

Oral antidepressants (e.g., amitriptyline, duloxetine) and anticonvulsants (e.g., pregabalin, gabapentin) are today's first choice for the treatment of neuropathic pain, and opioids (e.g., tramadol, oxycodone) are an example of today's second choice. However, the majority of patients is not compliant, most probably because of absence of expected effects or the induction of intolerable side effects, including sedation, dizziness, depression, nausea and constipation. Furthermore, the chronic use of such analgesics can induce drug-drug interactions as well as nephrotoxicity and hepatotoxicity. Unfortunately, despite partial pain relief through standard treatments, neuropathic pain may get worse over time.

Two commonly used topical analgesics are capsaicin (a vanilloid receptor agonist) and lidocaine (a voltage-gated sodium channel blocker). Capsaicin is thought to cause desensitization and denervation, the latter through reversible retraction of the nerve endings induced by TRPV1 receptor activation, leading to an overall long-term reduction of pain. Capsaicin 8% patch however, has the disadvantage that it increases burning and often needs to be combined with a local anesthetic, and that it has to be applied once every 3 months in a pain clinic. Its Numbers Needed to Treat (NNT) is disappointingly low, between 6 and 12. Topical capsaicin 0.025% to 0.075% cream has the disadvantage that it has to be applied 3 to 4 times daily during 5 to 6 weeks, its NNT is around 7, and considerable side effects such as burning, stinging or erythema complicate its use. Because capsaicin is lipophilic and usually is emulsified in a cream, thorough hand washing or the use of hand gloves is necessary not to irritate eyes and/or mucous membranes, all leading to decreases in patient compliance. Lidocaine inhibits voltage-gated sodium channels, and thus stabilizes the neuronal membrane potential of abnormally excitable peripheral nerve fibers. This results in a decrease of allodynia and hyperalgesia. Lidocaine 5% patch is registered for the treatment of neuropathic pain in several countries and its NNT is around 4. The patch needs to be replaced every 12 hours, with patch-free intervals of at least 12 hours and cannot be used on wounds, ulcers, damaged or inflamed skin, commonly seen in patients with diabetic neuropathy. Furthermore, especially in elderly, the plaster has to be cut in a correct shape. The handling therefore is complex and thus the compliance is suboptimal.

The main disadvantage of patches is that its application on various parts of the body is complicated due to the fixed and standard shape of the patch. Topical creams of the disclosure do not have this disadvantage, and are much easier to apply.

While endeavoring to find new effective and safe topical creams, it was discovered that the classical compound phenytoin, also known as diphenylhydantoin or 5,5-diphenyl-2,4-imidazolidinedione, administered as a topical cream of 5% or 10%, reduces neuropathic pain in a clinical meaningful way, without leading to side effects. While endeavoring to find new effective and safe topical creams, it was also discovered that the phenytoin, administered as a topical cream of 20%, reduces neuropathic pain in a clinical meaningful way, without leading to side effects. The cream is tested and shown to be effective in a number of patients who all were refractory for other analgesic therapies with good results (See section EXAMPLES, below). The working mechanism of the active pharmaceutical ingredient, i.e., the phenytoin, in the topical cream of the disclosure differs from the mechanism of action of local anesthetics, since patients treated with the cream of the disclosure do not report the common anesthetic effects after application, while they do report analgesic effects, with an action of onset between 3 and 30 minutes. The topical cream of the disclosure is effective in, e.g., 10 to 15 minutes after application of a cream of the disclosure with 10% phenytoin by weight, about 30 minutes after application of a cream of the disclosure with 5% phenytoin by weight (See section EXAMPLES, below), whereas pain emerged in 20 minutes after application of a cream of the disclosure.

The stability of the cream of the disclosure is also excellent and creams of the disclosure are stable for 12 months.

A second aspect of this disclosure relates to a method for preparing a pharmaceutical composition for use in the treatment of peripheral neuropathic pain, comprising the steps of:

a. providing oil-soluble constituents at between 20° C. and 95° C., and separately providing water soluble constituents of a pharmaceutically acceptable carrier for topical use;

b. providing an analgesic selected from phenytoin or a derivative, a prodrug, a stereoisomer, and/or a salt thereof, or any combination thereof, preferably phenytoin or phenytoin sodium or a combination thereof;

c. mixing the oil-soluble constituents at between 20° C. and 95° C. of step a. by stirring, and separately, dissolving the water-soluble constituents of step a. in water, wherein the water is optionally heated to between 20° C. and 95° C. while dissolving the water-soluble constituents of step a., thereby providing an aqueous solution;

d. combining the mixed oil-soluble constituents of step c. with the aqueous solution of step c., wherein the temperature of the mixed oil-soluble constituents and the aqueous solution is about the same, preferably about 70° C., and mixing by stirring, thereby providing the pharmaceutically acceptable carrier for topical use; and e. mixing the selected analgesic of step b. with the pharmaceutically acceptable carrier of step d. by adding the selected analgesic to the pharmaceutically acceptable carrier for topical use while stirring for between 5 and 20 minutes, preferably at about 20° C.; and f. optionally adjusting the pH of the aqueous solution to between 4.0 and 6.5 or to between 10.0 and 12.0.

A further aspect of this disclosure relates to a method for preparing a pharmaceutical composition for use in the treatment of peripheral neuropathic pain, comprising the steps of:

a. providing a pharmaceutically acceptable carrier for topical use, which pharmaceutically acceptable carrier is a cream;
b. providing an analgesic selected from phenytoin or a derivative, a prodrug, a stereoisomer, and/or a salt thereof, or any combination thereof, preferably phenytoin or phenytoin sodium or a combination thereof;
c. mixing the constituents of step a. and b. at a temperature of between 15° C. and 30° C., preferably about 18° C. in a high sheer mixer, preferably in the first half and 3 minutes at 500 rpm to 1000 rpm and subsequently 1 to 4 minutes at 1000 rpm to 2000 rpm;
d. repeating step c. for between 1 time and 8 times, preferably 3 times, with a pause of between 8 and 12 minutes, preferably 10 minutes between each round of mixing to let cool down the cream to room temperature; and
e. optionally adjusting the pH of the aqueous solution to between 4.0 and 6.5 or to between 10.0 and 12.0.

Figure 2:
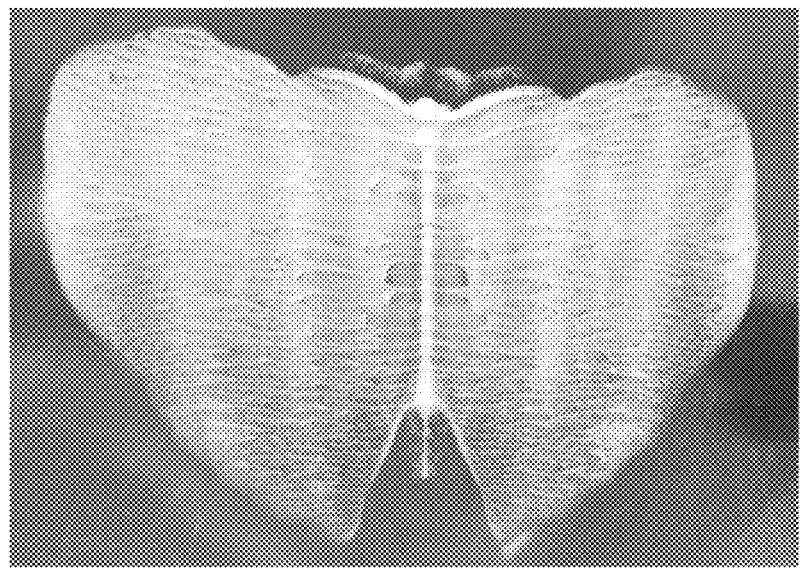
FIG. 2: Example of a cold mixed phenytoin 30% cream of the disclosure, i.e., mixed at room temperature without the provision of heat to the cream by any use of an external source of heat during mixing of the constituents of the cream, showing no grains.

In FIG. 2, a pharmaceutical composition prepared with the method here above is shown, providing the insight that such pharmaceutical composition is free of particulate matter, according to the disclosure. Surprisingly, the method here above provided a pharmaceutical composition of the disclosure lacking any visible particles and having beneficial smearability appropriate for topical use at the skin of a human patient.

In one embodiment, in the method according to the disclosure, the pharmaceutical composition is a pharmaceutical topical composition, and that use is the topical use in the treatment of peripheral neuropathic pain.

In one embodiment, in the method according to the disclosure, the pharmaceutical composition is a pharmaceutical topical composition, and that use is the topical use on the skin in the treatment of peripheral neuropathic pain in a human patient.

In one embodiment, in the method according to the disclosure, the pharmaceutical composition is a pharmaceutical topical composition, and the use of the composition in the treatment of peripheral neuropathic pain is the topical use on intact skin of the treated person in the treatment of peripheral neuropathic pain.

In one embodiment, in the method according to the disclosure, the pharmaceutical composition is a pharmaceutical topical composition, and the use of the composition in the treatment of peripheral neuropathic pain is the topical use on intact skin of the treated person in the treatment of peripheral neuropathic pain. Here, as already mentioned before, intact skin and healthy intact skin have their common scientific meaning and here refer to non-injured skin free of, e.g., ulcers, wounds, lesions, cuts, and refer to skin comprising a closed outer layer of epidermis.

In one embodiment, the method according to the disclosure is the method, wherein the pharmaceutical composition is a pharmaceutical topical composition, and wherein the use of the composition in the treatment of peripheral neuropathic pain is the topical use through the skin of the patient in the treatment of peripheral neuropathic pain.

In one embodiment, the method according to the disclosure is the method, wherein the use of the composition in the treatment of peripheral neuropathic pain is in the treatment of a human.

One embodiment of the disclosure is the method for preparing a pharmaceutical composition for use in the treatment of peripheral neuropathic pain according to the disclosure, wherein the analgesic is filtered through a fine-mesh screen of between 30 and 50 mesh, preferably about 40 mesh, before mixing the analgesic in step e. with the pharmaceutically acceptable carrier for topical use.

One embodiment of the disclosure is the method for preparing a pharmaceutical composition for use in the treatment of peripheral neuropathic pain according to the disclosure, wherein the analgesic is filtered through a sieve of about 40 mesh, before mixing the analgesic in step e. with the pharmaceutically acceptable carrier for topical use.

One embodiment of the disclosure is the method for preparing a pharmaceutical composition for use in the treatment of peripheral neuropathic pain according to the disclosure, wherein the pharmaceutically acceptable carrier for topical use is a cream, a gel, a dispersion, an emulsion, a foam, a mist, a mouth wash, a lotion, a salve, an ointment, a spray, an aerosol, an oil, a plaster, a patch, a suspension, or a suppository, preferably the pharmaceutically acceptable carrier for topical use is a cream.

Topical formulations of the disclosure are prepared according to the method of the disclosure. The base used in any of the topical creams according to the disclosure and described herein is any pharmaceutically acceptable carrier which is capable of dermal delivery of the active compounds contained within the pharmaceutical composition. By way of example, this are creams, gels, dispersions, emulsions, foams, mists, mouth washes, lotions, salves, ointments, oils, sprays, aerosols, suppositories, suspensions, plasters, patches and various passive and active topical devices for absorption through the skin and mucous membranes, according to the disclosure.

An oil-in-water emulsion providing a cream base is most preferred for general applications on the skin. A liquid such as a suspension or emulsion is desirable for treating the scalp. The base preferably includes conventional emulsifiers and emollients including alginates, glyceryl stearate, PEG-100 stearate, cetyl alcohol, propylparaben, butylparaben, sorbitols, polyethoxylated anhydrosorbitol monostearate, white petrolatum, triethanolamine, lanolin, cocoa butter, shea butter and the like.

For example, after dissolving phenytoin sodium in a base of cetomacrogol cream, the result was a stable formulation. In the cream of the disclosure a range of 1% to 10% phenytoin was dissolved such that a stable formulation of the disclosure was obtained. According to the disclosure, the pharmaceutical composition of the disclosure contains between 0.5% and 20% by weight of the analgesic, preferably between 3% and 15% by weight, more preferably between 5% and 10% by weight, most preferably about 5% or about 10% by weight.

According to the disclosure, the pharmaceutical composition of the disclosure preferably contains between 0.5% and 40% by weight of the analgesic, preferably between 3% and 35% by weight, more preferably between 5% and 20% by weight, most preferably about 5% or about 10% by weight or about 20% by weight.

Without wishing to be bound by theory, the three compounds of the cream of the disclosure, which are of lipophilic nature, and which are thereby facilitating the penetration of the lipophilic phenytoin in the various parts of the epidermis, according to the disclosure, are: Cera cetomacrogolis emulsificans, paraffinum liquidum, VASELINE® white petroleum jelly.

Exemplary compositions of the disclosure are non-exhaustingly described in the EXAMPLES section, in Table 2, Table 3, Table 4, Table 5 and Table 6. Exemplary compositions of the disclosure are also non-exhaustingly described in the EXAMPLES section, in Table 7, Table 8, Table 9 and Table 10. A summary of the Cases 1 to 14 is provided in Table 16, showing the fast onset of the pain relief after administration of a pharmaceutical compound of the disclosure to the skin of a human patient, the duration of the pain relief and the extent of pain relief provided by the composition, as experienced by the patient suffering from peripheral neuropathic pain. From Case 1 to 14 and further from the extended case study with 68 patients, as detailed below, it is apparent that the pharmaceutical composition of the disclosure provides for a surprisingly fast onset of the pain relief experienced by the patient, i.e., within 30 minutes, an extended duration of the pain relief, and an extent of the pain relief of often 4 or more on the NRS.

All compounds applied in a pharmaceutical composition of the disclosure are accurately weighed using an approved weighing scale. The required amount of water is measured using an approved cylindrical graduate. Optionally, the active pharmaceutical ingredient of the pharmaceutical composition of the disclosure (e.g., phenytoin sodium, phenytoin) is first filtered through a fine-mesh screen of between 30 and 50 mesh, and preferably through a mesh-screen of 40 mesh, into a mortar. The benefit of first filtering the active pharmaceutical ingredient, which has the tendency to agglomerate, is that, for example, the phenytoin or the phenytoin sodium is finely and homogenously distributed facilitating subsequent optimal dissolving in the selected formulation base. According to the method for preparing a pharmaceutical composition of the disclosure, the oil-soluble compounds are heated to a temperature of between 20° C. and 95° C. and mixed, for example, mixed together in a stainless steel bowl of a stirring device (phase A): (e.g., paraffinum liquidum, VASELINE® white petroleum jelly). Then, for example, ceteareth and cetostearyl alcohol, which are also first heated to a temperature of between 20° C. and 95° C., are added to the, e.g., paraffinum liquidum, VASELINE® white petroleum jelly. See in the EXAMPLES section for examples of applicable oil-soluble compounds of the disclosure. The water-soluble compounds of a cream base according to the disclosure (e.g., acidum ascorbicum, citric acid monohydrate, sodium hydroxide and sodium dihydrogen phosphate dehydrate) are added while mixing to water with a temperature of between 20° C. and 95° C. (phase B). Optionally, at this stage, the pH is adjusted to between 4.0 and 6.5, preferably at about 4.5 to 6.2, according to the method of the disclosure. Before combining Phase A and Phase B, and mixing Phase A and Phase B, the two phases are brought at about the same temperature, preferably the same temperature. The temperature of Phase A and Phase B before combining and mixing the phases is between room temperature and about 95° C., preferably between about 20° C. and about 95° C., more preferably the temperature is about 70° C. Phase B is slowly poured in phase A and cooled down while stirring until the temperature is, for example, decreased to about 56° C., preferably 56° C., according to the method of the disclosure. Alternatively, Phase B is slowly poured in phase A and cooled down while stirring until the temperature is, for example, decreased to about 20° C., preferably room temperature, according to the method of the disclosure. Herewith, the pharmaceutically acceptable carrier for topical use is provided, for application in the pharmaceutical composition of the disclosure. Then, (e.g., the active compound phenytoin sodium or phenytoin is added to the mixture, i.e., the pharmaceutically acceptable carrier for topical use, while stirring for between 5 and 20 minutes, preferably for about 10 minutes according to the method of the disclosure, for example, by using a high-shear homogenizer. The temperature is preferably about 20° C. or about room temperature during the adding of the active pharmaceutical ingredient to the pharmaceutically acceptable carrier. Optionally, at this stage, the pH is adjusted to between 4.0 and 6.5, preferably at about 4.5 to 6.2, according to the method of the disclosure, or the pH is adjusted to between 10.0 and 12.0, preferably at about 11.0 to 11.5, according to the method of the disclosure. The compositions of the disclosure are then, for example, packaged in 30 grams aluminum tubes and stored according to methods well-known in the art.

One embodiment of the disclosure is the method for preparing a pharmaceutical composition for use in the treatment of peripheral neuropathic pain according to the disclosure, wherein the pharmaceutically acceptable carrier has a pH of between 10.0 and 12.0, preferably about 11.3. Preferably, the cream of the disclosure having a pH of between 10.0 and 12.0, preferably about 11.3 and comprising, for example, phenytoin sodium, consists of Paraffinum liquidum, VASELINE® white petroleum jelly, Ceteareth-20, Cetostearyl alcohol, Sodium dihydrogen phosphate dehydrate, Acidum ascorbicum 1.5%, Sodium hydroxide and Aqua purificata. Equally preferable is the cream of the disclosure having a pH of between 10.0 and 12.0, preferably about 11.3 and comprising, for example, phenytoin sodium, and consisting of Cera cetomacrogolis emulsificans, Decylis oleas, Sorbitol 70% cristallisabile, Acidum ascorbicum and Aqua purificata. Preferably, the cream of the disclosure provided by the method of the disclosure comprises 5% by weight of the cream of the phenytoin sodium.

One embodiment of the disclosure is the method for preparing a pharmaceutical composition for use in the treatment of peripheral neuropathic pain according to the disclosure, wherein the pharmaceutically acceptable carrier comprised by the pharmaceutical composition of the disclosure comprises at least one skin penetration enhancer.

One embodiment of the disclosure is the method for preparing a pharmaceutical composition for use in the treatment of peripheral neuropathic pain according to the disclosure, wherein the at least one skin penetration enhancer is/are selected from decylis oleas, macrogol cetostearyl ether, cetostearyl alcohol, or any combination thereof.

One embodiment of the disclosure is the method for preparing a pharmaceutical composition for use in the treatment of peripheral neuropathic pain according to the disclosure, wherein the pharmaceutical composition contains between 0.5% and 20% by weight of the analgesic, preferably between 3% and 15% by weight, more preferably between 5% and 10% by weight. The analgesic is preferably phenytoin or phenytoin sodium or a combination thereof.

One embodiment of the disclosure is the method for preparing a pharmaceutical composition for use in the treatment of peripheral neuropathic pain according to the disclosure, wherein the pharmaceutical composition contains between 0.5% and 40% by weight of the analgesic, preferably between 3% and 30% by weight, more preferably between 5% and 20% by weight. The analgesic is preferably phenytoin or phenytoin sodium or a combination thereof.

One embodiment of the disclosure is the method for preparing a pharmaceutical composition for use in the treatment of peripheral neuropathic pain according to the disclosure, wherein the pharmaceutically acceptable carrier has a pH of between 4.0 and 6.5, preferably between 4.5 and 6.2, more preferably about 5.5. Preferably, the cream of the disclosure having a pH of between 4.0 and 6.5, for example, about 4.5 or, for example, about 6.2, and comprising, for example, phenytoin, consists of Cera cetomacrogolis emulsificans, Decylis oleas, Sorbitol 70% cristallisabile, Acidum ascorbicum and Aqua purificata. Equally preferable is the cream of the disclosure having a pH of between 4.0 and 6.5, for example, about 4.5 or, for example, about 6.2, and comprising, for example, phenytoin sodium, and consisting of Cera cetomacrogolis emulsificans, Decylis oleas, Sorbitol 70% cristallisabile, Acidum ascorbicum, Citric acid monohydrate and Aqua purificata. Preferably, the cream of the disclosure provided by the method of the disclosure comprises 5% by weight of the cream of the phenytoin or the phenytoin sodium.

One embodiment of the disclosure is the method for preparing a pharmaceutical composition for use in the treatment of peripheral neuropathic pain according to the disclosure, wherein the pharmaceutical composition contains about 5% or about 10% by weight of phenytoin or phenytoin sodium or a combination thereof.

One embodiment of the disclosure is the method for preparing a pharmaceutical composition for use in the treatment of peripheral neuropathic pain according to the disclosure, wherein the pharmaceutical composition contains about 5% or about 10% or about 20% by weight of phenytoin or phenytoin sodium or a combination thereof.

A third aspect of this disclosure relates to a pharmaceutical composition obtainable by the method of the disclosure.

A further aspect of the disclosure relates to a pharmaceutical composition obtainable by the method of the disclosure for use in the treatment of peripheral neuropathic pain.

In one embodiment, the pharmaceutical composition obtainable by the method of the disclosure contains between 3% and 15% by weight of the analgesic selected from phenytoin or a derivative, a prodrug, a stereoisomer, and/or a salt thereof, or any combination thereof, preferably phenytoin or phenytoin sodium or a combination thereof.

In one embodiment, the pharmaceutical composition obtainable by the method of the disclosure contains between 3% and 40% by weight of the analgesic selected from phenytoin or a derivative, a prodrug, a stereoisomer, and/or a salt thereof, or any combination thereof, preferably phenytoin or phenytoin sodium or a combination thereof.

An embodiment of the disclosure is the pharmaceutical composition according to the disclosure, containing phenytoin or phenytoin sodium or a combination thereof, and further either comprising paraffinum liquidum, VASELINE® white petroleum jelly, ceteareth-20, cetostearyl alcohol, or comprising cera cetomacrogolis emulsificans, decylis oleas, sorbitol pharmaceutically, and wherein the pharmaceutically acceptable carrier for topical use is a cream.

An embodiment of the disclosure is the pharmaceutical composition according to the disclosure, containing 0.5% to 20% by weight phenytoin or phenytoin sodium or a combination thereof. An embodiment of the disclosure is the pharmaceutical composition according to the disclosure, containing 3% to 15% by weight phenytoin or phenytoin sodium or a combination thereof, preferably 5% to 10% by weight, more preferably about 5% by weight or about 10% by weight.

An embodiment of the disclosure is the pharmaceutical composition according to the disclosure, containing 0.5% to 40% by weight phenytoin or phenytoin sodium or a combination thereof. An embodiment of the disclosure is the pharmaceutical composition according to the disclosure, containing 3% to 35% by weight phenytoin or phenytoin sodium or a combination thereof, preferably 5% to 20% by weight, more preferably about 5% by weight or about 10%, or about 20% by weight. As said before, the "% by weight" indicates the mass of the analgesic as a percentage of the weight of the pharmaceutical composition of the disclosure throughout the description and claims, unless indicated otherwise.

Experiments were performed to assess the feasibility of compounding phenytoin cream in the dose-range of 20% to 30% by weight of the phenytoin cream. In a Topitec Automatic machine container, a base amount of cetomacrogol cream was mixed with phenytoin, and subsequently additional cetomacrogol cream was added to create phenytoin cream in three different concentrations: 22.5%, 25% and phenytoin 30% cream by weight of the phenytoin cream. A batch of 100 grams was produced and stirred during 3 rounds of 1 minute at 500 rpm and subsequently 3 minutes at 1000 rpm; a pause of 10 minutes between each round of mixing, to allow the cream to cool down to room temperature, i.e., about 18° C. Surprisingly, it was found that this "cold mixing" in the dose-range 20% to 30% phenytoin by weight of the phenytoin cream resulted in a homogenous cream, without any visible grains or particles, aggregates, crystals, etc., in the cream (see FIG. 2). Spreadability and the feel was good and such that the cream was applicable for the treatment of patients by topical application of the cream at the human skin such that the phenytoin can migrate through the skin.

According to the disclosure, a topical formulation of the disclosure is administered at the skin, (e.g., the human skin, at a dose four times daily, preferably three times daily, more preferably twice daily, more preferably daily, most preferably every other day. According to the disclosure, a topical formulation of the disclosure is administered for a period of at least one year, or longer, preferably at least one month, more preferably at least one week, most preferably at least one day, to achieve a continuous decrease of peripheral neuropathic pain or eventually a complete relief from the pain, preferably peripheral neuropathic pain from group B, consisting of low to moderate grade of peripheral neurogenic inflammation. Typically, the amount of administered topical formulation, i.e., the cream for topical use containing phenytoin of the disclosure, is between 0.1 gram and 4 grams per application. Thus, according to the disclosure, the unit dose of the cream for topical use containing phenytoin of the disclosure is between about 0.1 gram and 4 grams. Preferably, the unit dose is between 0.5 gram and 3.6 grams of the cream of the disclosure, according to the disclosure.

One embodiment of the disclosure is the pharmaceutical composition for use in the treatment of peripheral neuropathic pain according to the disclosure, wherein a patient is instructed to apply the cream containing phenytoin of the disclosure 3 times daily with a maximum four FTUs, unless side effects appear. In case side effects would appear (which occurred seldom with the patients using the cream containing phenytoin of the disclosure), patients were instructed not to apply any cream on the skin area affected by neuropathic pain until side effects had disappeared. Thereafter, when side effects had disappeared, patients were instructed to apply half of the dose of phenytoin of the disclosure, to prevent re-occurrence of side effects, and patients were instructed to apply the cream containing phenytoin of the disclosure less frequently, according to the disclosure. When needed, patients were allowed to apply the cream containing phenytoin of the disclosure more than 3 times a day, preferably 4, 5, 6 or 7 times a day, preferably up to a maximum of 8 times a day, or even more often if desirable and applicable. If the peripheral neuropathic pain is still not managed by application of a pharmaceutical composition of the disclosure, even when a patient takes a dose for 8 times per day, such patients were allowed to increase the dose with an additional 2 to 4 FTUs per application of the cream containing phenytoin of the disclosure, according to the disclosure (thus, 4 to 6 FTUs per administration, with eight administrations per day, adding up to about 2 gram to about 3.6 gram of the pharmaceutical composition of the disclosure per administration, and about 16 gram to about 28.8 gram of the pharmaceutical composition of the disclosure per the eight administrations during one day, according to the disclosure). "Managed" in the context of the disclosure refers to any degree of pain relief experienced by the patient to whom a pharmaceutical composition of the disclosure is administered, such that the pain is bearable for the patient.

Although the foregoing methods and compositions have been described in some detail by way of illustration and example for purposes of clarity of understanding, it will be readily apparent to those of ordinary skill in the art in light of the teachings of these methods and compositions of the disclosure that certain changes and modifications may be made thereto without departing from the spirit or scope of the disclosure. The present disclosure is not to be limited in scope by the specific embodiments disclosed in the examples, which are intended as illustrations of a few aspects of the disclosure, and any embodiments that are functionally equivalent are within the scope of this disclosure. Indeed, various modifications of the disclosure in addition to those shown and described herein will become apparent to those skilled in the art and are intended to fall within the scope of the disclosure.

Thus, this disclosure is intended to cover any and all adaptations or variations of various embodiments and arrangements of the disclosure. Combinations of the above arrangements, and other arrangements not specifically described herein, will be apparent to those of skill in the art upon reviewing the above description. Therefore, it is intended that the disclosure is not be limited to the particular arrangement(s) disclosed as the best mode contemplated for carrying out this disclosure, but that the disclosure includes all embodiments and arrangements falling within the scope of the disclosure.

One embodiment of the disclosure is the pharmaceutical composition according to the disclosure, wherein the analgesic is phenytoin or phenytoin sodium, or a combination thereof, and/or wherein the analgesic is a phenytoin derivative, phenytoin prodrug, phenytoin stereoisomer, and/or salt thereof, selected from the group consisting fosphenytoin, hydroxyphenytoin, 5-(3-hydroxyphenyl)-5-phenylhydantoin, 5-phenyl-5-(4-hydroxyphenyl)hydantoin glucuronide, ropitoin, ropitoin hydrochloride, 5-(2-hydroxyphenyl)-5-phenylhydantoin, 5-(3,4-dihydroxy-1,5-cyclohexadien-1-yl)-5-phenylhydantoin, N-aminodiphenylhydantoin, 5-(3,4-dihydroxyphenyl)-5-phenylhydantoin, PC-796, 5-p-methylphenyl-5-phenylhydantoin, 1-acetyl-3-acetoxy-5',5-diphenylhydantoin, 3-hydroxymethylphenytoin N,N-dimethylglycine ester, 3-(hydroxymethyl)phenytoin N,N-dimethylaminoethyl carbonate, 5-(4-hydroxy-3-methoxyphenyl)-5-phenylhydantoin, 3-pentanoyl-5,5-diphenylhydantoin, 3-(2-propylpentanoyl)-5,5-diphenylhydantoin, 5,5-bis(4-hydroxyphenyl)hydantoin, 3-(hydroxymethyl)phenytoin, phenytoin dihydrodiol, 4-aminophenytoin, N,N-dichlorophenytoin, diphenylthiohydantoin, diphenylhydantoin-3-phenyltricarbonylchromium ethyl acetate, 5,5-diphenylhydantoin-3-valerate-bovine serum albumin, phenytoin-1-methylnicotininate, 2-cyanoguanidinophenytoin, phenytoin-bis-hydroxyisobutyrate, N-acetylphenytoin, diphenylhydantoic acid, N'-3-oxymethylglucuronide phenytoin, diphenylhydantil, 5-(4'-fluorophenyl)-5-phenylhydantoin, Azumolene, 5,5-bis(4-trifluoromethylphenyl)hydantoin, 5,5-bis(4-methylphenyl)hydantoin, 5,5-bis(4-methoxyphenyl)hydantoin, 5-(4-methoxyphenyl)-5-phenylhydantoin, and 5-(4-dimethylaminophenyl)-5-phenylhydantoin, and other 5,5-diphenylimidazolidine derivatives, or a combination thereof.

A fourth aspect of the disclosure relates to a pharmaceutical composition for use in the treatment of peripheral neuropathic pain according to the disclosure, wherein the pharmaceutical composition is provided by the method of the disclosure or wherein the pharmaceutical composition is a composition of the disclosure.

Without wishing to be bound by theory, in diabetic neuropathy, CIAP, SFN and CIPN, targets for treating the neuropathic pain are supposed to be residing in the skin, especially in the epidermis. Still without wishing to be bound by theory, these targets for treating the neuropathic pain that contribute to the mechanism of peripheral sensitization might be based on the interplay between three different players: the nerve endings of nociceptors, the keratinocytes and the immune-competent cells. All of these factors express sodium channels of different classes (NaV1.3-1.5, 1.7, 1.8). Therefore, since phenytoin and phenytoin sodium are broad-acting sodium-channel blocking agents in the compounded cream of the disclosure, developed for the topical treatment of neuropathic pain according to the disclosure, the sodium-channel blocking activity is at the basis of the efficiency and efficacy of the pharmaceutical composition of the disclosure for use in the treatment of peripheral neuropathic pain.

The present disclosure will be illustrated further by means of the following non-limiting Examples.

EXAMPLES

In the following exemplifying patient cases 1-14, described below, all patients suffered from a peripheral neuropathic pain according to group B. In the cases, the effect of topical phenytoin cream according to the disclosure in patients with peripheral neuropathic pain is demonstrated. The pharmaceutical compositions containing phenytoin according to the disclosure contained 5% or 10%, or 15% or 20% phenytoin by weight in the following examples.

Patients belonging to group A and group C were in most occasions found to be non-responders to phenytoin cream of the disclosure, exemplified by the following Cases 1A and 2A for patients in Group A and Case 1C for a patient in Group C:

Group A
1A. A patient suffering from neuropathy due to toxic vitamin B6 levels in the blood, due to overdosing, was a non-responder to phenytoin cream;
2A. A patient suffering from an alcoholic neuropathy was a non-responder to phenytoin cream; and Group C
1C. A patient suffering from an autoimmune polyneuropathy was a non-responder to phenytoin cream.

Case 1. Diabetic Neuropathic Pain

A 69-year-old man, suffered since 2007 from peripheral neuropathic pain in both fore feet due to diabetes mellitus type 2. He scored his average pain as 9 on the 11-point numerical rating scale (NRS). His pain was characterized by burning, electric shocks, tingling, pins and needles, allodynia when soft stroking, and hand in hand there was numbness (anesthesia dolorosa). Especially his allodynia in his left foot was bothering him in the night, and he scored this symptom with 10 on the NRS. Pregabalin 75 mg twice daily did not have any effect. The patient was administered a compounded ketamine 10% by weight cream (J. M. Keppel Hesselink and D. J. Kopsky, 2013). The result was a reduction of allodynia to 3 on the NRS. The reduction of pain lasted 6 hours, after which he woke up and had to apply the ketamine cream again. After application of phenytoin 5% by weight cream according to the disclosure the patient did not experience allodynia during the night anymore (0 on the NRS). Pain was reduced within 30 minutes after application and lasted for at least 12 hours.

The pharmaceutical composition of the disclosure containing 5% by weight phenytoin sodium in a topical cream further consisted of the skin penetration enhancer cetostearyl alcohol (6.9% by weight of the cream). The pH of the pharmaceutical composition was 11.3. The patient applied 0.5 FTU at each fore foot during each administration, i.e., in total about 0.5 gram to 0.6 gram of the cream, thus containing between about 0.025 gram and 0.03 gram of the phenytoin sodium. The patient applied the cream of the disclosure 2 times per day. The patient applied the cream of the disclosure during a period of 3 months. It is intended that the patient continues using the cream of the disclosure during his lifespan, i.e., for the rest of his life.

Case 2. Diabetic Neuropathic Pain

A 61-year-old man, suffering since 2007 from diabetes mellitus type 2 and hypothyroidism, was treated with metformin 500 mg three times daily and Thyrax, as well as with 1000 IE vitamin D. The patient had pain in both feet and scored 8 on the NRS. His sleep quality was very much disrupted due to the neuropathic pain. The characteristics of the neuropathic pain were burning, electric, tingling and pricking sensation.

Treatment started with 5% by weight phenytoin cream according to the disclosure, resulting for the first time since years in absence of pain during the night. The patient needed to apply the cream 3 times in 24 hours for obtaining sufficient analgesia, and analgesic effects started 1 hour after application. The cream reduced the pain with 50% to a mean value of 4 on the NRS. The pain became stable for weeks and his quality of life was much improved.

The pharmaceutical composition of the disclosure containing 5% by weight phenytoin sodium in a topical cream further consisted of the skin penetration enhancer cetostearyl alcohol (6.9% by weight of the cream). The pH of the pharmaceutical composition was 11.3. The patient applied 0.8 FTU at each foot during each administration, i.e., in total about 0.8 gram to 1.0 gram of the cream, thus containing between about 0.04 gram and 0.05 gram of the phenytoin sodium. The patient applied the cream of the disclosure 3 times per day. The patient applied the cream of the disclosure during a period of 4 months. It is intended that the patient continues using the cream of the disclosure during his lifespan, i.e., for the rest of his life.

Case 3. Neuropathic Pain Due to CIAP

A 71-year-old man, suffered since 2000 from CIAP pain in both feet and legs up to the knees. He scored the pain as 8 on the NRS. The pain was characterized as burning, tingling, numbness, hypoesthesia for touch and pin prick, and allodynia when soft stroking. Warmth and cold discrimination and ankle jerk reflexes were diminished; vibration sensation was absent at both metatarsalphalangeal first joints. Oral amitriptyline, duloxetine, pregabalin and tramadol induced too many side effects such as sedation, anxiety, sleeping disturbances and edema, to be of use. Upon treatment with phenytoin 5% by weight cream according to the disclosure, within 30 minutes the patient experienced around 50% pain reduction. After one month use of phenytoin 5% by weight cream he experienced a global pain reduction from 8 to 5 on the NRS. Especially the burning sensation was diminished: from 8 to 4 on the NRS. The pain reducing effect started 10 minutes after application with a total effect duration of 3.5 hours.

The pharmaceutical composition of the disclosure containing 5% by weight phenytoin sodium in a topical cream further consisted of the skin penetration enhancer cetostearyl alcohol (6.9% by weight of the cream). The pH of the pharmaceutical composition was 11.3. The patient applied 3 FTU at both feet and legs during each administration, i.e., about 1.5 gram to 1.8 gram of the cream, thus containing between about 0.075 and 0.09 gram of the phenytoin sodium. The patient applied the cream of the disclosure 3 to 4 times per day. The patient applied the cream of the disclosure during a period of 2.5 month. It is intended that the patient continues using the cream of the disclosure during his lifespan, i.e., for the rest of his life.

Case 4. Combined CIAP and CIPN

A 71-year-old man, suffered since 2008 from CIAP, which worsened after chemotherapy (vincristine), which chemotherapy was received for the treatment of a non-Hodgkin lymphoma diagnosed in 2010. The characterization of the pain in his feet and legs was tingling, pins and needles, electric shocks, burning and cramps with in the legs as well as anesthesia dolorosa. He scored the pain an 8 on the NRS. The following compounded creams were tested in the treatment regime of the patient: baclofen 5% by weight, amitriptyline 5% by weight and clonidine 0.2% by weight cream ((J. M. Keppel Hesselink, et al., 2014); (D. J. Kopsky and J. M. Hesselink, 2012); (D. J. Kopsky and J. M. Keppel Hesselink, 2013); (D. J. Kopsky, et al., 2012)). However, none of these creams could reduce the pain totally, though the patient experienced adequate analgesia. In 2013 prostate cancer was diagnosed for which he underwent local radiation therapy and he also received the anti-testosterone compound leuproreline (Eligard). His neuropathic pain in his right foot recurred and the prescribed analgesic creams lost most of their analgesic effects. Application of phenytoin 5% by weight cream according to the disclosure, however, reduced the tingling, pins and needles and burning pain within 20 minutes and the pain was reduced from 8 to 3 on the NRS. The patient also perceived a cooling effect of phenytoin 5% by weight cream, and the duration of the effect was longer than the duration observed with the other analgesic creams, i.e., lasting for at least 5 hours. The patient's sleep quality improved considerably. Before the use of phenytoin 5% by weight cream according to the disclosure he scored a 6 on the NRS measuring pain interference regarding his sleep (0 no interference, 10 complete interference). After application with phenytoin 5% by weight cream according to the disclosure he scored a 0 on the NRS, meaning his sleep was not disturbed anymore.

The pharmaceutical composition of the disclosure containing 5% by weight phenytoin sodium in a topical cream further consisted of the skin penetration enhancer cetostearyl alcohol (6.9% by weight of the cream). The pH of the pharmaceutical composition was 11.3. The patient applied 0.8 FTUs at the right foot during each administration, i.e., about 0.4 gram to 0.5 gram of the cream, thus containing between about 0.02 gram and 0.025 gram of the phenytoin sodium. The patient applied the cream of the disclosure 3 times per day. The patient applied the cream of the disclosure during a period of 2 months. It is intended that the patient continues using the cream of the disclosure during his lifespan, i.e., for the rest of his life.

Case 5. CIAP

A 74-year-old woman suffered since 2006 of CIAP pain in both feet. She characterized the pain as burning as well as numbness in the same area, and scored the pain with 6 on the NRS. The pain aggravated after walking. Pregabalin had too much side effects. Treating the patient with amitriptyline 10% by weight, baclofen 5% by weight, and lidocaine 3% by weight combined with isosorbidedinitrate 0.4% by weight cream did not give enough pain reduction (from 6 to 5 on the NRS). Phenytoin 5% by weight cream according to the disclosure reduced the burning pain from 6 to 1 on the NRS. Within 10 minutes after application of the cream pain diminished considerably, and the duration of the effect was 5 hours. The patient applied the cream 3 times daily. Because of the pain reduction her mood improved considerably and she was planning a vacation again.

The pharmaceutical composition of the disclosure containing 5% by weight phenytoin sodium in a topical cream further consisted of the skin penetration enhancer cetostearyl alcohol (6.9% by weight of the cream). The pH of the pharmaceutical composition was 11.3. The patient applied 1.4 FTU at both feet during each administration, i.e., about 0.7 gram to 0.8 gram of the cream, thus containing between about 0.035 gram and 0.04 gram of the phenytoin sodium. The patient applied the cream of the disclosure 3 times per day. The patient applied the cream of the disclosure during a period of 4 months. It is intended that the patient continues using the cream of the disclosure during her lifespan, i.e., for the rest of her life.

Case 6. Trigeminal Neuralgia

An 86-year-old woman suffered since years from severe trigeminal pain with burning and tingling sensations. Gamma-knife intervention, gabapentin, lidocaine 5% by weight patch, and duloxetine did not have any effect. Clonazepam 0.5 mg 3 times daily made life acceptable, though she scored her pain around the eye still with a 9 on the NRS. Ketamine 10% cream did reduce some of the sharp characteristics of the pain, but its effect was barely noticeable. However, ten minutes after application of phenytoin 10% by weight cream according to the disclosure the pain reduced from 9 to 5 on the NRS. She had to apply the cream frequently as the analgesic effect was lasting for one to several hours only. The burning and tingling sensations were reduced from 9-10 to 6-7 after applying the cream. The subjective feeling of stiffness around the mouth was reduced from 10 to 8. She continued using the cream for more than a year.

The pharmaceutical composition of the disclosure containing 10% by weight phenytoin sodium in a topical cream further consisted of the skin penetration enhancer cetostearyl alcohol (6.6% by weight of the cream). The pH of the pharmaceutical composition was 11.3. The patient applied 0.2 FTUs on the site of pain during each administration, i.e., about 0.1 gram to 0.2 gram of the cream, thus containing between about 0.01 gram and 0.02 gram of the phenytoin sodium. The patient applied the cream of the disclosure 5 to 8 times per day. The patient applied the cream of the disclosure during a period of more than a year. It is intended that the patient continues using the cream of the disclosure during her lifespan, i.e., for the rest of her life.

Case 7. Post Herpetic Neuralgia

An 83-year-old man, suffering for 2 years from thoracic post-herpetic neuralgia, scored his pain with a 7 to 8 on the NRS, while using pregabalin 600 mg daily. Lidocaine cream, capsaicin 8% by weight plaster, and amitriptyline had no effect on his pain. Single-blind treatment with 10% by weight ketamine cream compared to phenytoin 10% by weight cream according to the disclosure demonstrated superiority of the phenytoin cream. The pain reduction of 50% emerged within 20 minutes after application, lasting for around 4-6 hours.

The pharmaceutical composition of the disclosure containing 10% by weight phenytoin sodium in a topical cream further consisted of the skin penetration enhancer cetostearyl alcohol (6.6% by weight of the cream). The pH of the pharmaceutical composition was 11.3. The patient applied 0.5 FTUs in total at the parts of the inflicted skin during each administration, i.e., about 0.25 gram to 0.3 gram of the cream, thus containing between about 0.025 gram and 0.03 gram of the phenytoin sodium. The patient applied the cream of the disclosure 3 times per day. The patient applied the cream of the disclosure during a period of 4 months. It is intended that the patient continues using the cream of the disclosure during his lifespan, i.e., for the rest of his life.

Case 8. CIPN

A 48-year-old man, with acute leukemia was treated with mitroxantrone and etoposide in July 2014. The chemotherapy caused hand-foot syndrome (redness and edema), and neuropathic pain in the feet. He described his pain as burning, tingling, pins and needles, and scored pain with an 8.5 on the NRS in November 2015. Physical examination revealed hypoesthesia for pinprick and touch and allodynia. The pain was diagnosed as neuropathic pain due to chemotherapy. Amitriptyline 10% cream reduced pain considerably, scores on NRS decreased from 8.5 to 0. The only minor point of the amitriptyline 10% cream was that the neuropathic pain recurred after 1 to 1.5 hours. In October 2016, he scored his neuropathic pain with a 6 on the NRS and received additionally phenytoin 5% cream, which also resulted in complete disappearance of the neuropathic pain, though longer: 3.5 hours, with an onset of effect of 15 minutes after application.

The pharmaceutical composition of the disclosure containing 5% by weight phenytoin in a topical cream further consisted of the skin penetration enhancer decylis oleas (19% by weight of the cream). The pH of the pharmaceutical composition was 4.5. The patient applied 0.8 FTU on each foot, i.e., in total about 0.8 gram to 1.0 gram of the cream, thus containing between about 0.04 gram and 0.05 gram of the phenytoin. The patient applied the cream of the disclosure 3 times per day. The patient applied the cream of the disclosure during a period of 1 month. It is intended that the patient continues using the cream of the disclosure during his lifespan, i.e., for the rest of his life.

Case 9. CIPN

In May 2016 a 54-year-old woman, received chemotherapy treatment (bortezomib) because of immunoglobulin light chain (AL) amyloidosis. Due to neuropathic pain in both hands the treatment had to be stopped after 5 injections. The neuropathic pain in the hands diminished, however the patient developed neuropathic pain in both feet in May 2016. She described her pain as burning, painful cold, tingling, pins and needles. The patient received gabapentin 2000 mg daily, oxycodone 20 mg to 30 mg daily to reduce the pain, though scored still an 8 on the NRS in August 2016. Other medication, such as amitriptyline and tramadol did not have any analgesic effect. The patient had difficulties with sleeping due to the pain.

Physical examination revealed hypoesthesia for pinprick and touch and allodynia. The sensation of warm and cold was disrupted in her feet up to her ankles. She did not feel vibration from feet up to her knees. Her ankle jerk reflexes were absent.

Test applications with analgesic creams revealed that baclofen 5% cream had a more profound pain reducing effect compared to two other compounded analgesic creams: clonidine 0.2% cream and lidocaine 3% combined with isosorbide dinitrate 0.4% cream. The pain could be reduced to a 3 on the NRS, though allodynia was still present. Following ketamine 10% cream application, allodynia disappeared.

In September 2016, the patient received phenytoin 5% cream of the disclosure (prepared with phenytoin sodium) and was asked to compare the pain reduction of this new cream with baclofen 5% cream. Before application of both creams, she scored her pain 7 on the NRS. The time of onset was for baclofen 5% cream 20 minutes and for the phenytoin 5% cream 30 minutes. The patient scored her pain reduction for baclofen 5% cream from 7 to 3 on the NRS, and for phenytoin 5% cream from 7 to a surprisingly low value, i.e., 0 on the NRS. The duration of effect of phenytoin 5% cream was 4 hours. Three weeks later she received phenytoin 5% cream (prepared with phenytoin), with comparable results as the clinical benefits achieved by applying the phenytoin sodium 5% cream. This effect resulted in a reduction of prescribed oxycodone from 20 mg to 10 mg daily, and gabapentin from 2000 mg to 1600 mg daily.

In October 2016, she received phenytoin 10% cream of the disclosure in order to test whether a higher concentration of phenytoin resulted in a more profound effect. After application of the phenytoin 10% cream, the time of onset for analgesia decreased, and surprisingly as fast as within 10 to 15 minutes she experienced a reduction of pain from 7 to 0 on the NRS. Furthermore, duration of the effect was surprisingly increased from 4 hours after administration of the phenytoin 5% cream of the disclosure, up to 6 hours after administration of the phenytoin 10% cream of the disclosure.

The first pharmaceutical composition of the disclosure, containing 5% by weight phenytoin sodium in a topical cream further consisted of the skin penetration enhancer cetostearyl alcohol (6.9% by weight of the cream). The pH of this pharmaceutical composition was 11.3. The patient applied 0.5 FTU at each fore foot during each administration, i.e., in total about 0.5 gram to 0.6 gram of the cream, thus containing between about 0.025 gram and 0.03 gram of the phenytoin sodium. The patient applied the cream of the disclosure 3 times per day and during a period of 1 month.

The second pharmaceutical composition of the disclosure, containing 5% by weight phenytoin in a topical cream, further consisted of the skin penetration enhancer decylis oleas (19% by weight of the cream). The pH of the pharmaceutical composition was 4.5. The patient applied 0.5 FTU on each foot, i.e., in total about 0.5 gram to 0.6 gram of the cream, thus containing between about 0.025 gram and 0.03 gram of the phenytoin. The patient applied the cream of the disclosure 3 times per day, during a period of 1 month.

The third applied pharmaceutical composition of the disclosure containing 10% by weight phenytoin in a topical cream further consisted of the skin penetration enhancer decylis oleas (18% by weight of the cream). The pH of the pharmaceutical composition was 3.9. The patient applied 0.5 FTU on each foot, i.e., in total about 0.5 gram to 0.6 gram of the cream, thus containing between about 0.5 gram and 0.6 gram of the phenytoin. The patient applied the cream of the disclosure 2 times per day, during a period of 1 month. It is intended that the patient continues using phenytoin 10% cream of the disclosure during her lifespan, i.e., for the rest of her life.

Case 10. Compression Neuropathy

A 71-year-old woman suffered since 1976 of pain of the right forefoot due to a peripheral compression neuropathy (n. digitalis proprius). Despite nortriptyline 30 mg before night, she scored her pain a 9.5 on the NRS. The characteristics of the pain were burning, painful cold and numbness in the same area.

Physical examination revealed hypoesthesia for touch and pin prick. Echographic examination showed that the fat from the fat chambers under the metatarsal joints was herniating in the $3^{rd}$ webspace in the standing position which gave compression on the n. digitalis proprius. The n. digitalis proprius was mildly thickened (3.4 mm) on the echography.

Therapeutic phase: after application of phenytoin 10% cream the onset of analgesic effect was reported to be 10 minutes, and the pain was reduced from 9.5 to 6.5 on the NRS, with a duration of the analgesic effect of 3 hours. She told that she experiences 35% reduction of the pain.

Then, the patient received a tube containing phenytoin 20% cream. After application of this cream the pain was reduced from 9.5 to 4.5 on the NRS. The patient reported she experiences 55% reduction of the pain. The duration of pain relief was 4.5 hours. She applies the 20% cream 3 times daily, and does not experience side effects.

The patient stated that the duration of analgesic effect after application of phenytoin 20% cream was 6 hours, instead of 3.5 hours after applying phenytoin 10% cream. The patient continued applying 20% phenytoin cream 4 times daily to cover 24 hours, without experiencing side effects.

The pharmaceutical composition of the disclosure containing 20% by weight phenytoin sodium in a topical cream further consisted of the skin penetration enhancer decylis oleas (20% by weight of the cream). The pH of the pharmaceutical composition was 5.0. The patient applied 1 FTU at her right forefoot during each administration, i.e., in total about 0.5 gram to 0.6 gram of the cream, containing between about 0.1 gram and 0.12 gram of phenytoin. The patient applied the cream of the disclosure 4 times daily. The patient applied the cream of the disclosure during a period of 2 months. It is intended that the patient continues using the cream of the disclosure during her lifespan, i.e., for the rest of her life.

Case 11. Diabetic Neuropathic Pain

A-60-year old woman suffered since 2012 of neuropathic pain in both forefeet due to diabetes mellitus type II. She scored her pain a 10 on the NRS, and she described the pain with the following characteristics: burning, electric shocks, tingling, pins and needles, itch and in the same area numbness.

Physical examination revealed hypoesthesia for touch and pin prick, allodynia for soft stroking, warmth cold discrimination disrupted both forefeet, and ankle jerk reflexes were absent.

On the DN-4 screenings questionnaire for neuropathic pain she scored a 9 out of 10.

Previous analgesic duloxetine was stopped due to no effect and side effects, she gained 30 kilos. Other current medication is metformin 850 mg once daily.

At one day, a single-blind response test was performed comparing two active creams: on the left foot baclofen 5% cream and on the right foot phenytoin 5% cream. The patient experienced pain reduction in the right foot (phenytoin 5%), but no pain reducing effect in the left foot after the application of baclofen 5% cream. Thus, phenytoin 5% cream was prescribed for further subsequent use, which reduced the pain from 10 to 6 on the NRS with an onset of effect of 15 minutes and analgesic effect during 4 hours. The patient applied phenytoin 5% cream 3 to 4 times a daily, without experiencing side effects.

Starting after about nine months since the first single-blind response test here above described, the patient received phenytoin 10% cream. About six weeks later, the patient reported that she felt very well. The pain intensity was reduced from 10 to 2 on the NRS, with a duration of 6 hours, and the patient applied the cream now for 3 times daily. The onset of action remained 15 minutes. Thus, this case shows a clear dose-response effect in favor to phenytoin 10% cream, both on the level of pain reduction, as well as related to the duration of analgesia.

Case 12. N-of-1 Study SFN

The following case is reported in the context of a clinical single-blind N-of-1 study.

A 77-year-old woman suffered since 2012 from SFN, diagnosed by the neurologist. She experienced burning pain only at night in both feet and scored the pain a 6 on the NRS. In the same area numbness was present. Physical examination revealed diminished vibration sensation at the knees and absent vibration sensation at the ankles and metatarsal joints; ankle jerk reflexes were absent and knee reflexes diminished; warmth/cold discrimination was absent up to 10 cm under the knees; hypoesthesia for pin prick and touch was present, up to 20 cm under the knees. The patient stopped the use of pregabalin because of too much side effects.

She subsequently started with application of phenytoin 10% cream before going to bed. She reported that administering the phenytoin 10% cream often resulted in a pain reduction of 50%, from 6 to 3 on the NRS within 10 minutes application, with a duration of around 3.5 hours. She needed to apply phenytoin 10% cream once more during the night, because of the short duration of effect.

In order to get a more consistent picture she was entered in an N-of-1 single-blind study, starting at day 0. The burning pain at that time was only present during the night. This single-blind study compared four different doses of phenytoin: 5%, 10%, 15%, 20% and placebo cream, provided in test tubes numbered 4, 1, 2, 5 and 3, respectively. The patient was asked to score the pain on the NRS, and pain interference on sleep (0 no interference, 10 complete interference), a subscale from the Brief Pain Inventory. The patient was instructed to apply cream from the test tubes before going to bed, not having yet the pain. Every three consecutive days she applied cream from the same test tube, starting with number 1, and ending with number 5. The total duration of the study was 15 days. She received escape therapy, a tube containing 10% phenytoin cream of which she already knew what the effect was. The following order of phenytoin and placebo creams was tested: 10%, 15%, placebo, 5% and 20%.

TABLE 1

| Cream | Pain NRS (3.00 a.m.) | pain interference on sleep on NRS | Extra application at 3.00 a.m. |
|---|---|---|---|
| Before application | 5 | 5 | |
| Placebo | 5 | 5 | yes |
| 5% | 4 | 4 | yes |
| 10% | 5 | 5 | yes |
| 15% | 5 | 5 | yes |
| 20% | 3.5 | 1.5 | no |

The first night without applying phenytoin 10% cream she scored her pain a 5 on the NRS and pain interference on sleep. All consecutive nights, she applied the cream around 23.30. At 3.00 a.m., she always woke up from the pain and/or needing to go to the toilet. Then she observed the pain intensity and pain interference on sleep and wrote her findings down. After application of placebo, 5%, 10% and 15%, the patient needed to apply the escape phenytoin 10% cream at 3.00 a.m. (See Table 1).

After applying phenytoin 20% cream, the patient scored her pain at 3.00 a.m. a 3.5 on the NRS, and pain interference on sleep was clearly reduced to 1.5 on the NRS. She did not need to apply the escape phenytoin 10% cream at 3.00 a.m. after application of phenytoin 20% cream. She noted that the duration of analgesia after applying the phenytoin 20% cream was around 7 hours.

Thus, the single-blind N-of-1 study revealed that application phenytoin 20% cream resulted in longest duration of analgesia (7 hours) and least interference with her sleep.

In a subsequent new open trial patient received tubes of 10%, 15% and 20% to observe the effect when applying phenytoin 10% cream on one leg and 15% or 20% cream on the other leg. The patient compared the effects of the different creams, knowing what she used. She reported on day 77 that there is no clear difference in effect between phenytoin 10% and 15% cream.

Hereafter, she compared phenytoin 10% and 20% cream, each on a different foot. She then reported a clear difference in favor of phenytoin 20% cream. She then chose to apply phenytoin 20% cream during the following days, and clearly did not need to use the escape cream anymore. She did not report any side effects after application of all creams.

The pharmaceutical composition of the disclosure containing 20% by weight phenytoin sodium in a topical cream further consisted of the skin penetration enhancer decylis oleas (20% by weight of the cream). The pH of the pharmaceutical composition was 5.0. The patient applied 0.5 FTU at each fore foot during each administration, i.e., in total about 0.5 gram to 0.6 gram of the cream, thus containing between about 0.1 gram and 0.12 gram of the phenytoin. The patient applied the cream of the disclosure once daily. The patient applied the cream of the disclosure during a period of 2 months. It is intended that the patient continues using the cream of the disclosure during her lifespan, i.e., for the rest of her life.

Example: Pharmaceutical Compositions of the Disclosure without a Skin Penetration Enhancer Efficacy and efficiency with regard to the treatment of peripheral neuropathic pain are demonstrated for two pharmaceutical compositions of the disclosure, wherein the two compositions do not comprise any skin penetration enhancer. Compounding and clinical effects of two formulations: 10% phenytoin by weight of the pharmaceutical composition according to the disclosure, in petrolatum, and 10% phenytoin by weight of the pharmaceutical composition according to the disclosure, in carbomer gel.

To compound 100 grams of phenytoin 10% petrolatum formulation (Table 14): add 10 g phenytoin powder to 30 g of petrolatum, and mix. Heat the mixture until melting point of petrolatum (around 50° C.) to ease the mixing. Mix, until no grains are present. The concentration of phenytoin in the homogenous paste after the first round of mixing is 40% phenytoin by weight of the composition. Subsequently, a further 70 g of petrolatum is added, heated up until melting point and mixed again until a homogenous substance is reached. Let the substance cool down while steering. The result was a homogenous white formulation, with good smearability properties and which induced desired clinical effects, as described below for Case 13.

To compound phenytoin 10% gel (Table 15), the following protocol was applied for preparing a pharmaceutical composition of the disclosure without skin penetration enhancer: mix in one jar carbomer 974P, edetate disodium and trometamol (powder mix). Mix in another jar aqua purificata with propylene glycol. Disperse the powder mix in the liquid aqua purificata/propylene glycol mix. Allow swelling time of 15 minutes. Add phenytoin powder. Mix all ingredients.

Case 13. CIAP

A 73-year-old man suffered from CIAP with complaints of burning pain in the lower legs, especially the feet. The average pain score, characterized as burning and pins and needles, was 7 to 8 on the NRS. The pain aggravated when sitting and lying in bed.

During the consultation, he experienced burning feet and scored his pain as 3 on the NRS. A single-blind placebo response test was performed. On the right foot placebo cream (1 FTU) was applied and on the left foot the phenytoin 10% petrolatum (1 FTU) as described here above (Table 14), was applied. The information given by the physician was: "One topical formulation can help to lessen your suffering without knowing how it exactly works. The other topical formulation I would like to offer you to test for the other foot, the working mechanism is clearer. After 30 minutes I will come back to evaluate the effect of both topical formulations."

After 2 minutes, the analgesic effect of the phenytoin 10% petrolatum was noticed. He scored the pain in his left foot as 0.5 on the NRS and the right foot (placebo) as 2.5 on the NRS. Clearly phenytoin 10% petrolatum had a more pronounced pain reduction of 2.5 points on the NRS compared to placebo, which only led to a pain reduction of 0.5 point on the NRS. Subsequently phenytoin 10% cream according to the composition listed in table 6 was applied on the right foot (on which placebo was applied earlier) in the previous response test. Within 2 minutes the onset of pain reduction was noticeable, and when the physician returned after 20 minutes the patient reported a pain reduction of 2.5 points in the NRS. Clearly, phenytoin 10% petrolatum and phenytoin 10% cream with a penetration enhancer had comparable effects as to onset of action and same analgesic effect. The duration of the analgesic effect was for both compositions also comparable: 5 to 6 hours.

The pharmaceutical composition of the disclosure containing 10% by weight phenytoin in petrolatum was free of any skin penetration enhancers. The patient applied 2 FTU at both feet during each administration, i.e., about 1 gram to 1.2 gram of the topical analgesic, containing between about 0.1 gram and 0.12 gram of the phenytoin. It is intended that the patient continues using the analgesic formulation of the disclosure during his lifespan, i.e., for the rest of his life, with the instruction to apply the topical analgesic up to 4 times a day.

These results show that the presence of any skin penetration enhancer in the pharmaceutical composition of the disclosure is not a requirement for the pharmaceutical composition inducing a beneficial effect in the patient with regard to reducing peripheral neuropathic pain.

Case 14. CIPN

A 72-year-old man suffered since June 2017 of CIPN, with neuropathic pain in both feet due to oxaliplatin treatment of a colon carcinoma. He scored his pain as 8 on the NRS, and the pain was characterized as: electric shocks, pins and needles, tingling, and numbness in the same area. Physical examination revealed absence of vibration sensation up to the knees, no knee and ankle jerk reflexes, hypoesthesia for pinprick and allodynia in both feet. Also warmth cold discrimination was disrupted in both feet.

A single-blind placebo response test was performed. On the left foot placebo cream (1 FTU) was applied and on the right foot phenytoin 10% gel (1 FTU) was applied. The phenytoin 10% gel was the gel as here above described (Table 15). The instruction given by the physician was: "One topical formulation can help to lessen your suffering without knowing how it exactly works. The other topical formulation I would like to offer you to test for the other foot, the working mechanism is clearer. After 30 minutes I will come back to evaluate the effect of both topical formulations."

After 15 minutes, the analgesic effect of the phenytoin 10% gel was noticed. The pain in the area on which phenytoin 10% gel was applied was reduced from 8 to 5.5 on the NRS, and the pain in area on which placebo cream was applied was reduced from 8 to 7 on the NRS. Thus, phenytoin 10% gel clearly led to a pain reduction in neuropathic pain.

These results show that the presence of any skin penetration enhancer in the pharmaceutical composition of the disclosure is not a requirement for the pharmaceutical composition inducing a beneficial effect in the patient with regard to reducing peripheral neuropathic pain.

The pharmaceutical composition of the disclosure containing 10% by weight phenytoin in the topical gel was applied by the patient as 2 FTU at both feet during each administration, i.e., about 1 gram to 1.2 gram of the gel, thus containing between about 0.1 gram and 0.12 gram of the phenytoin. It is intended that the patient continues using the gel of the disclosure during his lifespan, i.e., for the rest of her life with the instruction to apply the topical analgesic up to 6 times a day.

Case 15. Efficacy of 20% and 30% Phenytoin Cream in Diabetic Neuropathic Pain

A 58-year-old female suffered from diabetes mellitus type 1, treated with insulin, levothyroxine, glimepiride, metformin, enalapril, rosuvastatin, and as analgesics both paroxetine 60 mg and gabapentin 1200 mg daily. Previously, she had responded relatively well on various topical creams, such as amitriptyline 10%, ketamine 10%, and gabapentin 10% cream, though after some years the analgesic response was reduced. At the time, she re-entered the clinic, she was treated with ketamine 10% cream, because she suffered quite badly from allodynia, and ketamine 10% cream seemed to be able to reduce this symptom. However, the pain slowly crept back to a baseline score of 7 to 8 on the NRS and she asked whether a new analgesic cream could help her.

The patient received an equal amount (e.g., fingertip unit: 0.5 gram) of placebo cream and phenytoin 10% cream of the disclosure for applying in this case at the right foot respectively the left foot, and subsequently phenytoin 30% cream of the disclosure on the right foot again (the placebo-treated foot before the cross-over).

The given instruction before applying the creams was: "I would like to offer you to test 2 creams on the pain areas, which I believe can help to lessen your suffering without knowing how one cream exactly works. The working mechanism of the other cream is clearer, though side effects can occur. After maximal 30 minutes, you will tell us whether there is a difference in pain scoring on the NRS, and based on your evaluation we know what best to prescribe you."

After the application of both creams, the patient stated within 10 minutes there was only a 1.5 on the NRS difference on the area where the placebo-cream was applied, without her being able to exactly describe this difference. The foot felt warmer, and therefore somewhat less painful. The patient did not have any pain reduction in the area on which the phenytoin 10% cream of the disclosure was applied on, therefore she was a non-responder.

Subsequently, a cross-over treatment to the application of phenytoin 30% cream of the disclosure on the "placebo" foot was established, and within 5 minutes the patient reported an initial decrease of pain from 6.5 to 3.5 on the NRS, eventually leading to a decrease of 1 to 1.5 on the NRS. Subsequently, the patient switched from being administered phenytoin 30% cream of the disclosure to applying phenytoin 20% cream of the disclosure for further treatment. After 2 weeks, she informed the physician that pain after application of phenytoin 20% cream of the disclosure decreased consequently to 1 to 1.5. It is thus concluded that for this case phenytoin 20% cream of the disclosure was as effective as phenytoin 30% cream of the disclosure when the extent of pain relief for the patient is considered.

Exemplary Compositions According to the Disclosure

TABLE 2

| Phenytoin sodium 5% by weight cream (100 gram) | |
| --- | --- |
| Phenytoin sodium | 5 g |
| Paraffinum liquidum | 5.7 g |
| VASELINE ® white petroleum jelly | 14.3 g |
| Ceteareth-20 | 1.7 g |
| Cetostearyl alcohol | 6.9 g |
| Sodium dihydrogen phosphate dehydrate | 0.3 g |
| Acidum ascorbicum 1.5% | 0.15 g |
| Sodium hydroxide | 0.05 g |
| Aqua purificata | 65.9 g: add to 100 grams |
| pH is 11.3 | |

TABLE 3

| Phenytoin sodium 10% by weight cream (100 gram) | |
| --- | --- |
| Phenytoin sodium | 10 g |
| Paraffinum liquidum | 5.4 g |
| VASELINE ® white petroleum jelly | 13.5 g |
| Ceteareth-20 | 1.6 g |
| Cetostearyl alcohol | 6.6 g |
| Sodium dihydrogen phosphate dehydrate | 0.3 g |
| Acidum ascorbicum 1.5% | 0.15 g |
| Sodium hydroxide | 0.05 g |
| Aqua purificata | 62.4 g: add to 100 grams |
| pH is 11.3 | |

TABLE 4

| Phenytoin sodium 5% by weight cream (100 gram) | |
| --- | --- |
| Phenytoin sodium | 5 g |
| Cera cetomacrogolis emulsificans | 14.2 g |
| Decylis oleas | 19 g |
| Sorbitol 70% cristallisabile | 3.8 g |
| Acidum ascorbicum | 0.18 g |
| Aqua purificata | 57.82 g/add to 100 g |
| pH is 11.3 | |

TABLE 5

| Phenytoin 5% by weight cream (100 gram) | |
| --- | --- |
| Phenytoin | 5 g |
| Cera cetomacrogolis emulsificans | 14.2 g |
| Decylis oleas | 19 g |
| Sorbitol 70% cristallisabile | 3.8 g |
| Acidum ascorbicum | 0.18 g |
| Aqua purificata | 57.82 g/add to 100 g |
| pH is 4.5 | |

TABLE 6

| phenytoin 10% by weight cream (100 gram) Phenytoin 10% by weight cream (100 gram) | |
| --- | --- |
| Phenytoin | 10 g |
| Cera cetomacrogolis emulsificans | 13.5 g |
| Decylis oleas | 18 g |
| Sorbitol 70% cristallisabile | 3.6 g |
| Acidum ascorbicum | 0.17 g |
| Aqua purificata | 55.73 g/add to 100 g |
| pH is 3.9 | |

TABLE 7

| Phenytoin sodium 5% by weight cream (100 gram) | |
| --- | --- |
| Phenytoin sodium | 5 g |
| Cera cetomacrogolis emulsificans | 14.3 g |
| Decylis oleas | 19 g |
| Sorbitol 70% cristallisabile | 3.8 g |
| Acidum ascorbicum | 0.2 g |
| Citric acid monohydrate | 0.128 |
| Aqua purificata | 57.572 g/add to 100 g |
| pH is 6.2 | |

TABLE 8

| Phenytoin 20% by weight cream (100 gram) | |
| --- | --- |
| Phenytoin | 20 g |
| Cera cetomacrogolis emulsificans | 12 g |
| Decylis oleas | 16 g |
| Sorbitol 70% cristallisabile | 3.2 g |
| Acidum ascorbicum | 0.2 g |
| Aqua purificata | 48.6 g/add to 100 g |
| pH is 5.0 | |

TABLE 9

| Phenytoin 30% by weight cream (100 gram) | |
| --- | --- |
| Phenytoin | 30 g |
| Cetearyl alcohol | 8.4 g |
| Ceteareth-20 | 2.1 g |
| Decylis oleas | 14 g |
| Sorbitol 70% cristallisabile | 2.8 g |
| Acidum ascorbicum | 0.2 g |
| Aqua purificata | 42.5 g/add to 100 g |
| pH is 5.16 | |

TABLE 10

| Phenytoin 10% by weight cream (100 gram) | |
| --- | --- |
| Phenytoin | 10 g |
| Cetearyl alcohol | 8.4 g |
| Ceteareth-20 | 2.1 g |

TABLE 10-continued

| Phenytoin 10% by weight cream (100 gram) | |
| --- | --- |
| Decylis oleas | 14 g |
| Sorbitol 70% cristallisabile | 2.8 g |
| Acidum ascorbicum | 0.2 g |
| SLM 2026 containing: Aqua, Caprylic/Capric Triglyceride, Hydrogenated Phosphatidylcholine, Pentylene Glycol, Glycerin, *Butyrospermum Parkii* Butter, Squalene, Ceramide NP | 20 g |
| Aqua purificata | 42.5 g/add to 100 g |
| pH is 5.35 | |

Without wishing to be bound by theory, the three compounds of the above-listed creams of the disclosure in Tables 2-10, which are of lipophilic nature, and which are thereby facilitating the penetration of the lipophilic phenytoin in the various parts of the epidermis, according to the disclosure, are: Cera cetomacrogolis emulsificans, paraffinum liquidum, VASELINE® white petroleum jelly.

Example: Phenytoin Cream and Phenytoin Sodium Cream for the Treatment of 68 Patients Suffering from Neuropathic Pain Neuropathic pain is disabling and usually difficult to treat. Guidelines for neuropathic pain treatment only provide for a limited number of therapies, and the numbers needed to treat most interventions are disappointing—between 6 and 10—indicating that many patients remain in pain even after prescribing various analgesics currently available. More than half of the currently treated patients discontinue the use of neuropathic pain medication within one year, most probably due to side effects and/or disappointing clinical results. Up to now only lidocaine 5% plaster and capsaicin 8% plaster are registered for the treatment of neuropathic pain. Capsaicin 8% plaster, however, has to be applied in an outward patient clinic every three months, and lidocaine 5% plaster is troublesome in handling, especially when applied on the feet of elderly patients.

In a 3-year period, detailed clinical information was gathered on patients suffering from neuropathic pain and treated with a pharmaceutical composition of the disclosure, on a regular basis. The clinical data relating to this treated cohort, which consists of 68 patients who were treated with cream comprising 5% phenytoin by total weight of the cream ("phenytoin 5%," "phenytoin sodium 5%") and/or cream comprising 10% phenytoin by total weight of the cream ("phenytoin 10%," "phenytoin sodium 10%"), is presented below.

Material and Methods

Data from the 68 patients using the aforementioned phenytoin 5% or phenytoin 10% cream was gathered for 44 months. Pain intensity was measured on the 11-point numerical rating scale (NRS). Descriptive statistics were used for socio-demographic data, diagnoses, and pain characteristics. The screenings tool for neuropathic pain (DN-4: Douleur Neuropathique, 4 questions) was used to determine the pain characteristics. Pre-test/post-test comparisons on a per protocol basis were performed using Wilcoxon signed-rank tests. The number of patients achieving minimum efficacy criteria (MEC) of pain relief over a baseline of 30% (moderate benefit: MEC30) and 50% (considerable benefit: MEC50) measured on the NRS, were calculated. The independent t-test analyzes differences between 2 different groups (phenytoin 10% and phenytoin 5% users) was used. The statistical analysis was performed in SPSS 22 (SPSS Inc., Chicago, Ill., USA). For the sake of the early identification of responders, a single-blind response test was developed. This single-blind response test was simple and took only a minute to conduct. First, the baseline pain with NRS of 2 areas (e.g., both feet) was documented. Patients would than administer an equal amount of placebo cream and active cream on the 2 different areas with separate hands to avoid contamination. When a patient experienced a minimal pain reduction of 2 points difference in reduction on the NRS between active cream and placebo cream within 30 minutes, they were identified as a responder on phenytoin 10% cream. Plasma was collected for the determination of phenytoin levels in a sub-cohort of 16 patients. Blood was taken around T-max, between 1 and 3 hours after the application of the cream.

Results

From January 2014 to October 2017, the patients were treated with phenytoin sodium 5% and phenytoin sodium 10%, or phenytoin 5% and phenytoin 10% cream. In total, 63 patients were treated and treatment and treatment results were documented in detail. Most patients were diagnosed by a neurologist as having chronic pain due to peripheral neuropathy. Thirty-two patients were male (50.8%) and 31 (49.2%) were female. The age of the patients ranged between 43 and 89 years, with a mean age of 68.0 years (SD: 10.5). The diagnoses of those patients treated with phenytoin 5% or phenytoin 10% cream are summarized in Table 11. Seven patients used phenytoin (sodium) 5% cream, and 56 patients used (sodium) 10% cream.

An open or single-blind response test was performed in most patients. To date, the patients described in this cohort are being treated during a period of a few weeks to 34 months, nearly all without experiencing any side effects.

Patients experiencing certain neuropathic pain characteristics as defined by the DN-4 are presented in Table 12. Forty-four (70%) patients experienced 3 or more neuropathic pain characteristics.

Table 13 summarizes various parameters related to application of phenytoin cream.

TABLE 11

| Diagnoses of neuropathic pain patients | | |
| --- | --- | --- |
| Diagnosis | Phenytoin 5% N (%) | Phenytoin 10% N (%) |
| Total patients | 7 (100) | 56 (100) |
| Diabetic type II polyneuropathy | 2 (28.6) | 8 (14.3) |
| Chronic Idiopathic Axonal Polyneuropathy | 4 (57.1) | 11 (19.6) |
| Peripheral neuropathy e.c.i. | 1 (14.3) | 9 (16.1) |
| Small Fiber Neuropathy | | 8 (14.3) |
| Chemotherapy Induced Polyneuropathy | | 6 (10.7) |
| Post-Herpetic Neuralgia | | 6 (10.7) |
| Peripheral neuropathy due to Lyme disease | | 1 (1.8) |
| Trigeminal neuralgia | | 1 (1.8) |
| Meralgia Paresthetica | | 1 (1.8) |
| Post toxic axonal polyneuropathy | | 1 (1.8) |
| Traumatic neuropathy | | 1 (1.8) |
| Radiculopathy | | 1 (1.8) |
| Compression neuropathy | | 1 (1.8) |
| Plexopathy | | 1 (1.8) |

TABLE 12

Pain characteristics of neuropathic pain

| Pain characteristics | Phenytoin 5% N (%) | Phenytoin 10% N (%) |
|---|---|---|
| Burning | 7 (100) | 47 (83.9) |
| Painful cold | 1 (14.3) | 12 (21.4) |
| Electric shocks | 2 (28.6) | 15 (26.8) |
| Tingling | 6 (85.7) | 35 (62.5) |
| Pins and needles | 5 (71.4) | 39 (69.6) |
| Itch | 1 (14.3) | 9 (16.1) |
| Allodynia | 2 (28.6) | 21 (37.5) |
| Cramps | 0 (0) | 5 (8.9) |

TABLE 13

Use and effect characteristics of phenytoin cream

| Use characteristics and effect | Phenytoin 5% Mean (SD), [range] | Phenytoin 10% Mean (SD), [range] |
|---|---|---|
| Times of daily application | 2.5 (0.9) [1.0-3.5] | 2.3 (1.3) [0.1-7.0] |
| Grams per application | 0.8 (0.3) [0.6-1.2] | 0.9 (0.9) [0.2-6.7] |
| Grams of daily application | 1.8 (0.6) [0.9-2.4] | 1.8 (1.4) [0.1-6.7] |
| Onset of action (minutes) | 18.0 (19.3) [3-60] | 15.7(14.3) [2-60] |
| Duration of effect (hours) | 5.4 (2.2) [3.5-10] | 8.7 (10.0) [1-70] |
| Duration of use (months) | 3.3 (2.7) [1-9] | 3.0 (4.9) [1-36] |
|  | N (%) | N (%) |
| 30% pain reduction on NRS | 7 (100) | 51 (91.1) |
| 50% pain reduction on NRS | 5 (71.4) | 40 (71.4) |

The mean onset of action (onset to perceptible pain relief) after application was about 15 minutes for both phenytoin 5% cream and phenytoin 10% cream. The mean duration of analgesia was almost 5 hours for phenytoin 5% cream, while patients treated with phenytoin 10% cream reported a mean duration of meaningful analgesia of almost 9 hours. The difference of 3.3 hours between the 2 groups was not significant (t(59)=0.9, p=0.4), using the independent t-test.

Only 2 patients reported local side effects: transient aggravation of a burning sensation, and in one patient red papules after administration of phenytoin 10% cream, though in that case not after the application of phenytoin 5% cream. These side effects were transient and disappeared after stopping treatment.

Plasma samples were taken after several days of the application of phenytoin 10% cream in 16 patients.

Phenytoin plasma levels were measured after the application of phenytoin 10% cream in 16 patients. Most patients applied the phenytoin cream for 1 to 2 weeks to reach a steady state mean days of application (SD), [range]: 14 (25.1), [1-104]. The mean (SD) [range] daily amount of phenytoin 10% cream was 1.4 grams (1.5) [0.3-6.7]. Plasma sampling was performed, usually 1.5 to 3 hours after last application of the cream, with mean duration in hours (SD), [range]: 2.3 (1.8), [0.5-8.5]. Surprisingly, no phenytoin plasma levels were detected (below the limit of detection), even after the application of 6.7 grams of phenytoin 10% cream in one case. This formulation can thus be characterized as an epidermal formulation.

The patient data show that phenytoin cream is helpful in the treatment of neuropathic pain. The fast onset of action of the phenytoin cream enables differentiation of responders from non-responders ("stratification") via a single-blind response test based on placebo cream and active cream comprising the phenytoin or the phenytoin sodium, applied on two different areas of skin. This method has the advantage that active analgesic cream of the disclosure comprising the phenytoin or the phenytoin sodium, is administered to responders only, and thus the method provides the advantage of being able to individualize therapy directed specifically to each patient. Furthermore, such targeted prescription will reduce the chances that patients would end up as non-responders to the cream, after an initial placebo response of some weeks. For most oral neuropathic pain medication, the onset of action takes days to weeks, which onset of action is thus much longer than the onset of action experienced with phenytoin cream of the disclosure. Both capsaicin 8% plaster and oral pregabalin have a median onset of action (>30% pain reduction) of 7.5 days and 36 days, respectively.

Another study showed that pregabalin showed a significant pain reduction at day 2. Also at day 2, gastro-retentive gabapentin showed significantly more pain relief than placebo. For the lidocaine 5% patch, the onset of action was reported within 4 hours. Thus the onset of action of an average of 15 minutes is very fast, when compared to methods of treatment currently available. Without wishing to be bound by theory, the fast onset of action of the pharmaceutical composition of the disclosure might be due to the effects of phenytoin on the nerve endings in the epidermis, and also to the possible effect on the keratinocytes and the immune competent cells, which all known to cross-talk with the nerve endings and nociceptors.

The percentage of patients experiencing a pain reduction of at least 50% on the NRS is around 65%.

The average duration of the analgesic effect of phenytoin 10% is over 8 hours, which corresponds with a mean daily application of 2.3 times. Patients can therefore apply phenytoin cream of the disclosure in the morning and evening, and if needed also at noon, to cover the whole day.

No systemic adverse effects have been reported. This finding is in line with the fact that phenytoin plasma levels were below the limit of detection in 16 patients of the data-pool of patients treated with a pharmaceutical composition of the disclosure. Only 2 patients reported local adverse events: transient aggravation of burning sensation, and in one patient red papules after administration of phenytoin 10% cream, though in that case not after the application of phenytoin 5% cream of the disclosure. These adverse events were transient and disappeared after stopping treatment.

Phenytoin cream of the disclosure is safe and is effective in a cohort of 63 patients suffering from neuropathic pain. Since most of the patients previously were non-responders or partial responders to analgesic interventions described in the Guidelines, the data show that such cream of the disclosure is effective and efficient for the treatment of peripheral neuropathic pain. In most patients the onset of action is fast, around 15 minutes. This is of particular interest, since administration of most oral analgesics may take days to weeks before sufficient pain reduction is reached. Furthermore, the fast onset of action makes a single-blind placebo controlled response test possible. Thus, this single-blind placebo controlled response test enables the clinician to identify responders directly at the first visit and to subsequently prescribe the cream of the disclosure. Such an approach, together with the fast onset of action, also contributes to enhancement of the compliance. Side effects were rare.

Constituents and their amounts in two exemplary pharmaceutical compositions of the disclosure wherein skin penetration enhancers are not included, which compositions are efficient and efficacious in reducing peripheral neuropathic pain when topically administered to the skin of patients.

TABLE 15

| Phenytoin 10% by weight gel (100 gram) | |
| --- | --- |
| Phenytoin | 10 g |
| Carbomer 974P | 0.9 g |
| Edetate disodium | 0.09 g |
| Propylene glycol | 9 g |
| Trometamol | 0.9 g |
| Aqua purificata | 79.11 g |
| pH is 6.83 | |

Summary of Results of Case 1-14

In the Table 16 below, a summary is provided of the efficiency of the pharmaceutical compositions of the disclosure administered topically on the skin of human patients suffering from peripheral neuropathic pain.

TABLE 16

Results of treating peripheral neuropathic pain patients with pharmaceutical compositions of the disclosure - Case 1-14
Results of treating peripheral neuropathic pain patients with pharmaceutical compositions of the disclosure - Case 1-14

| Case | Pharmaceutical composition | Onset of pain reduction after administration | Extent of pain reduction on the NRS | Duration of pain reduction |
| --- | --- | --- | --- | --- |
| 1 | 5 wt % phenytoin cream | 30 minutes | From 3 to 0 | At least 12 hours |
| 2 | 5 wt % phenytoin cream | 1 hour | From 8 to 4 | About 8 hours |
| 3 | 5 wt % phenytoin cream | 10 minutes | From 8 to about 4 to 5 | 3.5 hours |
| 4 | 5 wt % phenytoin cream | 20 minutes | From 8 to 3 (pain); from 6 to 0 (sleep interference) | 5 hours (pain); overnight (sleep interference) |
| 5 | 5 wt % phenytoin cream | 10 minutes or less | From 6 to 1 | 5 hours |
| 6 | 10 wt % phenytoin cream | 10 minutes | From 9 to 5 (pain); from 9-10 to 6-7 (burning and tingling sensations) | 1 to a few hours |
| 7 | 10 wt % phenytoin cream | 20 minutes or less | From 7-8 to 3-4 | 4 to 6 hours |
| 8 | 5 wt % phenytoin cream | 15 minutes | From 6 to 0 | 3.5 hours |
| 9 | 5 wt % phenytoin cream | 30 minutes | From 7 to 0 | 4 hours |
| 9 | 10 wt % phenytoin cream | Within 10-15 minutes | From 7 to 0 | 6 hours |
| 10 | 10 wt % phenytoin cream | 10 minutes | From 9.5 to 6.5 | 3 to 3.5 hours |
| 10 | 20 wt % phenytoin cream | n.a. | From 9.5 to 4.5 | 4.5 to 6 hours |
| 11 | 5 wt % phenytoin cream | 15 minutes | From 10 to 6 | 4 hours |
| 11 | 10 wt % phenytoin cream | 15 minutes | From 10 to 2 | 6 hours |
| 12 | 10 wt % phenytoin cream | 10 minutes | From 6 to 3 | 3.5 hours |
| 12 | 20 wt % phenytoin cream | n.a. | From 5 to 3.5 (pain); from 5 to 1.5 (pain interference on sleep) | About 7 hours |
| 13 | 10 wt % phenytoin composition without skin penetration enhancer | 2 minutes | From 3 to 0.5 | 5 to 6 hours |
| 14 | 10 wt % phenytoin gel without skin penetration enhancer | 15 minutes | From 8 to 5.5 | About 4 hours |

The pharmaceutical compositions of Table 14 and Table 15 relate to the Case 13 and Case 14, respectively, outlined in detail here above.

TABLE 14

| Phenytoin 10% by weight petrolatum (100 gram) | |
| --- | --- |
| Phenytoin | 10 g |
| Petrolatum | 90 g |

Aspects of Small Molecule Compounds

In Table 17, some skin penetrating compounds are listed.

TABLE 17

| small-molecule compounds capable of penetrating the skin. | | |
| --- | --- | --- |
| Active compound | Dalton | Log P |
| Phenytoin | 252 | 2.5 |
| Amitriptyline | 277 | 4.9 |
| Ketamine | 238 | 2.9 |

TABLE 17-continued small-molecule compounds capable of penetrating the skin.

| Active compound | Dalton | Log P |
|---|---|---|
| Baclofen | 214 | 1.3 |
| Clonidine | 230 | 1.6 |
| Loperamide | 477 | 5.5 |
| Lidocaine | 234 | 2.6 |
| Isosorbide dinitrate | 236 | 1.3 |

Single-Blind Response Test with Phenytoin 10% Cream in 20 Patients

Here above, it has been described that, for example, 5%, 10% and 20% phenytoin cream is efficient and efficacious in treating peripheral neuropathic pain when applied topically to the skin of human patients. Onset of pain relief is within 30 minutes, and patients report a positive effect on sleep when a pharmaceutical composition of the disclosure is administered topically on their skin.

Results in Brief of a Single-Blind Placebo-Controlled Response Test Assessing Efficacy of a Pharmaceutical Composition of the Disclosure In a single-blind placebo-controlled response test with 20 patients suffering from peripheral neuropathic pain, the efficacy of phenytoin 10% cream was assessed amongst other parameters. Most of the patients suffered from symmetrical peripheral neuropathic pain, with at least a pain score of 3 on the 11-point numerical rating scale (NRS). In this single-blind response test, patients compared the analgesic effect of phenytoin 10% to placebo cream, which was applied on different pain areas usually on both feet. The response was defined as a 2-point difference in pain reduction as measured by the NRS between areas on which phenytoin 10% cream and placebo cream was applied. The responders were subsequently prescribed phenytoin 10% cream. Of the 20 patients, 75% were responders to phenytoin 10% cream. The mean reduction as measured with the NRS in the phenytoin 10% cream area was 3.4 (SD: 1.3) and in the placebo cream area 1.2 (SD: 1.2). The difference of the mean percentage pain reduction between phenytoin 10% cream and placebo cream was 37.0% (SD: 23.1, $p<0.001$). When taking a 50% reduction on the NRS as a full response criterion, there were 60% responders on phenytoin 10% cream and only 10% responders on placebo cream. The single-blind response test helped the patients and their clinicians to fast identify the appropriate treatment and contributed to the establishment of personalized medicine.

Results in Detail of the Single-Blind Placebo-Controlled Response Test Assessing Efficacy of a Pharmaceutical Composition of the Disclosure In total, 20 patients were entered into the single-blind placebo-controlled response test. Nine patients were female (45%) and 11 patients were male (55%). The age of the patients ranged between 49 and 89 years, with a mean age of 66.2 years (SD: 9.6). The diagnoses are summarized in Table 18. Most of the patients (N=12, 60%) experienced neuropathic pain only in both feet; other locations are summarized in Table 19. The duration of the neuropathic pain ranged between 1 and 150 months, with a mean duration of 47.4 months (SD: 43.5).

TABLE 18

Diagnosis.

| Diagnosis | N |
|---|---|
| Idiopathic peripheral neuropathy | 6 |
| CIAP | 4 |
| CIPN | 3 |
| DM type II neuropathy | 2 |
| SFN | 2 |
| PHN | 1 |
| Post Guillain Barre | 1 |
| HMSN type 2 | 1 |

The mean reduction on the NRS in the phenytoin 10% area was 3.4 (SD: 1.3) and in the placebo area 1.2 (SD: 1.2). The difference of the mean percentage pain reduction between phenytoin 10% cream and placebo cream was 37.0% (SD: 23.1, $p<0.001$). A Wilcoxon signed rank test showed that there was a significant difference ($Z=-3.828$, $p<0.001$) between scores. In total, 75% of the patients experienced at least a 2 point pain reduction difference on the NRS in favor of phenytoin 10% cream. An exact McNemar's test determined that there was a statistically significant difference in the proportion of MEC50 after application of phenytoin 10% cream and placebo cream, $p=0.002$ (see Table 20). The same holds true for MEC30, $p<0.001$ (see Table 3).

TABLE 19

Location of neuropathic pain.

| Locations | N |
|---|---|
| Both feet | 12 |
| Both feet and lower legs | 6 |
| Complete legs and feet | 1 |
| Right upper leg | 1 |

TABLE 20

Comparisons of effect between phenytoin 10% and placebo cream application.

|  | Phenytoin 10% | Placebo NRS |
|---|---|---|
| Pre-treatment NRS (SD) | 6.2 (1.5) | 6.0 (1.5) |
| Post-treatment NRS (SD) | 2.9 (1.8) | 4.8 (1.7) |
| Mean pain reduction % (SD) | 56.8% (22.9)† | 19.8% (17.6) |
| MEC50% [N] | 60% [12]* | 10% [2] |
| MEC30% [N] | 90% [18]** | 25% [5] |
| Mean onset of effect in minutes (SD) [N] | 15.4 (9.5) [20] | 17.8 (9.5) [12] |

†$p < 0.001$ with Wilcoxon signed rank test
*$p = 0.002$ with the McNemar's test,
**$p < 0.001$ with the McNemar's test In 6 patients from this cohort of 20 patients, phenytoin plasma levels were determined after 1 to 2 weeks of phenytoin 10% cream application. Plasma sampling was performed 1.5 to 3 hours after the last application. No phenytoin plasma levels were detected (below the limit of detection). In 10 other patients no plasma levels were detected even after the application of 6.7 grams of phenytoin 10% cream in one case.

References

Babaei S., Ghanbarzadeh S., Adib Z. M., Kouhsoltani M., Davaran S., Hamishehkar H. Enhanced skin penetration of lidocaine through encapsulation into nanoethosomes and nanostructured lipid carriers: a comparative study. Pharmazie. 2016; 71(5):247-51.

Bailey D. N. Percutaneous absorption of tricyclic antidepressants: amitriptyline, nortriptyline, imipramine, and desipramine. J. Anal. Toxicol. 1990; 14(4):217-218.

Bos J. D., Meinardi M. M. The 500 Dalton rule for the skin penetration of chemical compounds and drugs. Exp. Dermatol. 2000; 9(3):165-9.

Callaghan, B. C., R. S. Price, K. S. Chen & E. L. Feldman (2015). The Importance of Rare Subtypes in Diagnosis and Treatment of Peripheral Neuropathy: A Review. *JAMA Neurol.,* 72, 1510-8.

Derry, S., P. J. Wiffen, R. A. Moore & J. Quinlan (2014). Topical lidocaine for neuropathic pain in adults. *Cochrane Database Syst Rev,* 7, Cd010958.

Ellis, A. & D. L. Bennett (2013). Neuroinflammation and the generation of neuropathic pain. *Br. J. Anaesth.,* 111, 26-37.

Glinn, M. A., A. J. Lickteig, L. Weber, S. Recer, M. Salske, A. Harvey, B. Rappold, J. Stensland & P. Bell (2017). Urinary Concentrations of Topically Administered Pain Medications. *J. Anal. Toxicol.* 41, 127-133.

Jay, G. W. & R. L. Barkin (2014). Neuropathic pain: etiology, pathophysiology, mechanisms, and evaluations. *Dis. Mon.,* 60, 6-47.

Keppel Hesselink, J. M. & D. J. Kopsky (2013). Treatment of chronic regional pain syndrome type 1 with palmitoylethanolamide and topical ketamine cream: modulation of nonneuronal cells. *J. Pain Res.,* 6, 239-45.

Keppel Hesselink, J. M., D. J. Kopsky & N. L. Sajben (2014). Vulvodynia and proctodynia treated with topical baclofen 5% and palmitoylethanolamide. *Arch. Gynecol. Obstet,* 290, 389-93.

Keskin G. et al. Doxepin incorporated into a dermatologic cream: an assessment of both doxepin antipruritic action and doxepin action as an inhibitor of papules, in allergen and histamine-caused pruritus. Allergol. Immunopathol. (Madr) 1999; 27(5):265-70.

Kopsky, D. J. & J. M. Hesselink (2012). High doses of topical amitriptyline in neuropathic pain: two cases and literature review. *Pain Pract.,* 12, 148-53.

Kopsky, D. J. & J. M. Keppel Hesselink (2013). Neuropathic pain as a result of acromegaly, treated with topical baclofen cream. *J. Pain Symptom Manage.,* 46, e4-5.

Kopsky, D. J., R. Liebregts & J. M. Keppel Hesselink (2012). Central neuropathic pain in a patient with multiple sclerosis treated successfully with topical amitriptyline. *Case Rep. Med.,* 2012, 471835.

Korinth G, Wellner T, Schaller K H, Drexler H. Potential of the octanol-water partition coefficient (log P) to predict the dermal penetration behaviour of amphiphilic compounds in aqueous solutions. Toxicol. Lett. 2012; 215(1): 49-53.

L. Lund G. Alvan A. Berlin B. Alexanderson. Pharmacokinetics of single and multiple doses of phenytoin in man. European Journal of Clinical Pharmacology March 1974, Volume 7, Issue 2, pp 81-86

Moulin, D., A. Boulanger, A. J. Clark, H. Clarke, T. Dao, G. A. Finley, A. Furlan, I. Gilron, A. Gordon, P. K. Morley-Forster, B. J. Sessle, P. Squire, J. Stinson, P. Taenzer, A. Velly, M. A. Ware, E. L. Weinberg & O. D. Williamson (2014). Pharmacological management of chronic neuropathic pain: revised consensus statement from the Canadian Pain Society. *Pain Res. Manag.,* 19, 328-35.

Petersen B1, Rovati S. Diclofenac epolamine (Flector) patch: evidence for topical activity. Clin. Drug Investig. 2009; 29(1):1-9.

Rajabally, Y. A., D. Adams, P. Latour & S. Attarian (2016). Hereditary and inflammatory neuropathies: a review of reported associations, mimics and misdiagnoses. *J. Neurol. Neurosurg. Psychiatry.*

Serajuddin, A. T. & C. I. Jarowski (1993). Influence of pH on release of phenytoin sodium from slow-release dosage forms. *J. Pharm. Sci.,* 82, 306-10.

Tse S. et al. Skin permeability and pharmacokinetics of diclofenac epolamine administered by dermal patch in Yorkshire-Landrace pigs. J. Pain Res. 2012; 5:401-8.

Uceyler, N., W. Kafke, N. Riediger, L. He, G. Necula, K. V. Toyka & C. Sommer (2010). Elevated proinflammatory cytokine expression in affected skin in small fiber neuropathy. *Neurology,* 74, 1806-13.

Uceyler, N., N. Riediger, W. Kafke & C. Sommer (2015). Differential gene expression of cytokines and neurotrophic factors in nerve and skin of patients with peripheral neuropathies. *J. Neurol.,* 262, 203-12.

Uceyler, N., J. P. Rogausch, K. V. Toyka & C. Sommer (2007). Differential expression of cytokines in painful and painless neuropathies. *Neurology,* 69, 42-9.

Vincent, A. M., B. Calabek, L. Roberts & E. L. Feldman (2013). Biology of diabetic neuropathy. *Handb. Clin. Neurol.,* 115, 591-606.

The invention claimed is:

1. A method for treating peripheral neuropathic pain due to small fiber neuropathy, diabetic neuropathy type 1 and 2, chronic idiopathic axonal polyneuropathy, post-herpetic neuralgia, trigeminus neuralgia, chemotherapy induced polyneuropathy, a traumatic neuropathy, compression neuropathy, or an infectious neuropathy in remission, the method comprising:
applying a pharmaceutical composition to intact skin free of ulcers, wounds, and cuts of a human in need thereof, such that the pain is reduced,
wherein the pharmaceutical composition comprises an analgesic as the active pharmaceutical ingredient and a pharmaceutically acceptable carrier, and
wherein the analgesic is selected from the group consisting of phenytoin and/or a salt thereof.

2. The method according to claim 1, wherein the analgesic is phenytoin or phenytoin sodium or a combination thereof.

3. The method according to claim 1, wherein the pharmaceutical composition comprises a pharmaceutically acceptable carrier for topical use selected from the group consisting of a cream, a gel, a dispersion, an emulsion, a foam, a mist, a lotion, a salve, an ointment, a spray, an aerosol, an oil, and a suspension.

4. The method according to claim 1, wherein the pharmaceutical composition is a cream.

5. The method according to claim 1, wherein the pharmaceutical composition is applied between eight times daily to once every other day.

6. The method according to claim 1, wherein the pharmaceutical composition is applied once every other day.

7. The method according to claim 1, wherein the pharmaceutical composition is administered for a period of at least one month.

8. The method according to claim 1, wherein the pharmaceutical composition is chronically administered.

9. The method according to claim 1, wherein the analgesic has a unit dose of between 0.0005 gram and 2.0 grams.

10. The method according to claim 1, wherein the pharmaceutical composition contains between 3% and 40% by weight analgesic.

11. The method according to claim 1, wherein the pharmaceutical composition contains between 5% and 20% by weight analgesic.

12. The method according to claim 1, wherein the pharmaceutically acceptable carrier further comprises at least one skin penetration enhancer.

13. The method according to claim 12, wherein the at least one skin penetration enhancer is selected from the group consisting of decylis oleas, macrogol cetostearyl ether, cetostearyl alcohol, and any combination thereof.

14. The method according to claim 1, wherein the pharmaceutical composition further comprises paraffinum liquidum, white petroleum jelly, ceteareth-20, and/or cetostearyl alcohol.

15. The method according to claim 1, wherein the pain is at least caused by a localized low to moderate grade of peripheral neurogenic inflammation.

16. The method according to claim 15, wherein the pain is at least caused by a localized low to moderate grade of peripheral neurogenic inflammation in and around the sensory afferents in the skin, the nociceptors, and the tissue around the afferents.

17. A method for treating peripheral neuropathic pain due to small fiber neuropathy, diabetic neuropathy type 1 and 2, chronic idiopathic axonal polyneuropathy, post-herpetic neuralgia, trigeminus neuralgia, chemotherapy induced polyneuropathy, a traumatic neuropathy, compression neuropathy, or an infectious neuropathy in remission, the method comprising:
   applying a pharmaceutical composition to intact skin free of ulcers, wounds, and cuts of a human in need thereof, such that the pain is reduced,
   wherein the pharmaceutical composition comprises an analgesic as the active pharmaceutical ingredient and a pharmaceutically acceptable carrier,
   wherein the analgesic is phenytoin and/or a salt thereof, and
   wherein the phenytoin and/or a salt thereof does not penetrate the blood of the human.

18. A method for treating peripheral neuropathic pain due to small fiber neuropathy, diabetic neuropathy type 1 and 2, chronic idiopathic axonal polyneuropathy, post-herpetic neuralgia, trigeminus neuralgia, chemotherapy induced polyneuropathy, a traumatic neuropathy, compression neuropathy, or an infectious neuropathy in remission, the method comprising:
   applying a pharmaceutical composition to intact skin free of ulcers, wounds, and cuts of a human in need thereof, such that the pain is reduced,
   wherein the pharmaceutical composition comprises an analgesic as the active pharmaceutical ingredient and a pharmaceutically acceptable carrier,
   wherein the analgesic is phenytoin and/or a salt thereof, and
   wherein the phenytoin and/or a salt thereof is not detectable in the blood of the human.

* * * * *